(12) United States Patent
Tonkovich et al.

(10) Patent No.: US 8,497,308 B2
(45) Date of Patent: Jul. 30, 2013

(54) INTEGRATED MICROCHANNEL SYNTHESIS AND SEPARATION

(75) Inventors: Anna Lee Y. Tonkovich, Dublin, OH (US); Robert D. Litt, Westerville, OH (US); Timothy M. Werner, Traverse City, MI (US); Bin Yang, Columbus, OH (US)

(73) Assignee: Velocys, Inc., Plain City, OH (US)

( * ) Notice: Subject to any disclaimer, the term of this patent is extended or adjusted under 35 U.S.C. 154(b) by 583 days.

(21) Appl. No.: 12/439,872

(22) PCT Filed: Sep. 5, 2007

(86) PCT No.: PCT/US2007/019352
§ 371 (c)(1),
(2), (4) Date: Jul. 1, 2010

(87) PCT Pub. No.: WO2008/030467
PCT Pub. Date: Mar. 13, 2008

(65) Prior Publication Data
US 2010/0280136 A1 Nov. 4, 2010

Related U.S. Application Data

(63) Continuation-in-part of application No. 11/516,027, filed on Sep. 5, 2006, now Pat. No. 7,820,725.

(51) Int. Cl.
*C07C 27/00* (2006.01)
(52) U.S. Cl.
USPC .......................................... 518/700; 518/706
(58) Field of Classification Search
USPC ....................................................... 518/706
See application file for complete search history.

(56) References Cited

U.S. PATENT DOCUMENTS

| | | | |
|---|---|---|---|
| 5,072,789 A | 12/1991 | Usui et al. |
| 5,089,532 A | 2/1992 | King et al. |
| 5,262,443 A | 11/1993 | Topsoe et al. |
| 5,311,935 A | 5/1994 | Yamamoto et al. |
| 5,611,214 A | 3/1997 | Wegeng et al. |
| 5,811,062 A | 9/1998 | Wegeng et al. |
| 6,192,596 B1 | 2/2001 | Bennett et al. |
| 6,490,812 B1 | 12/2002 | Bennett et al. |
| 6,509,085 B1 | 1/2003 | Kennedy |
| 6,666,909 B1 | 12/2003 | TeGrotenhuis et al. |
| 6,680,044 B1 | 1/2004 | Tonkovich et al. |
| 6,766,817 B2 | 7/2004 | da Silva |
| 6,869,462 B2 | 3/2005 | TeGrotenhuis et al. |
| 6,875,247 B2 | 4/2005 | TeGrotenhuis et al. |
| 6,918,404 B2 | 7/2005 | da Silva |
| 6,969,505 B2 | 11/2005 | Tonkovich et al. |
| 7,014,835 B2 | 3/2006 | Mathias et al. |
| 7,066,586 B2 | 6/2006 | da Silva |
| 7,084,180 B2 | 8/2006 | Wang et al. |
| 7,217,741 B2 | 5/2007 | Bowe et al. |
| 7,234,514 B2 | 6/2007 | Vogel |
| 2003/0116016 A1 | 6/2003 | Monzyk et al. |
| 2003/0131729 A1 | 7/2003 | Tonkovich et al. |
| 2004/0034111 A1 | 2/2004 | Tonkovich et al. |
| 2004/0105812 A1 | 6/2004 | Tonkovich et al. |
| 2004/0266615 A1 | 12/2004 | Watson et al. |
| 2005/0133457 A1 | 6/2005 | Tonkovich et al. |
| 2005/0175519 A1 | 8/2005 | Rogers, Jr. et al. |
| 2005/0176832 A1 | 8/2005 | Tonkovich et al. |
| 2006/0016215 A1 | 1/2006 | Tonkovich et al. |
| 2006/0016216 A1 | 1/2006 | Tonkovich et al. |
| 2006/0180298 A1 | 8/2006 | Egawa et al. |
| 2007/0197382 A1 | 8/2007 | West |

FOREIGN PATENT DOCUMENTS

| | | |
|---|---|---|
| JP | 2006 247828 A | 9/2006 |
| WO | WO 01/95237 A2 | 12/2001 |
| WO | WO 01/95237 A3 | 10/2002 |
| WO | WO 03/078052 A1 | 9/2003 |
| WO | WO 2006/079848 A1 | 8/2006 |
| WO | WO 2007/096699 A2 | 8/2007 |
| WO | PCT/US07/19352 | 5/2008 |
| WO | PCT/US07/19352 | 4/2009 |

OTHER PUBLICATIONS

Unknown, Commercial-Scale Demonstration of the Liquid Phase Methanol (LPMEOH) Process, DOE/FE-0470, Project Performance Summary Clean Coal Technology Demonstration Program, Jun. 2004, Air Products Liquid Phase Conversion Company, Allentown, PA.

Unknown, Petrochemical Processes 2005 Handbook, Gulf Publishing Company, USA.

*Primary Examiner* — Shawquia Young
(74) *Attorney, Agent, or Firm* — Taft Stettinius & Hollister LLP

(57) ABSTRACT

A process for carrying out at least two unit operations in series, the process comprising the step of: (a) directing a feed stream into an integrated assembly which comprises a first microchannel unit operation upon at least one chemical of the feed stream to generate a distributed output stream that exits the first microchannel unit operation in a first set of discrete microchannels isolating flow through the discrete microchannels; and (b) directing the distributed output stream of the first microchannel unit operation into a second microchannel unit operation as a distributed input stream, to continue isolating flow between the first set of discrete microchannels, and conducting at least one operation upon at least one chemical of the input stream to generate a product stream that exits the second microchannel unit operation, where the first microchannel unit operation and the second unit operation share a housing.

25 Claims, 28 Drawing Sheets

| Rxn # | | | A | E, KJ/mol |
|---|---|---|---|---|
| 1 | 3H2+CO→ H2O+CH4 | $R_{CH_4} = k_1 \exp(E_1/RT)C_{H_2}^1$ | 2.289E12 | 160 |
| 2 | 5H2+2CO→ 2H2O+C2H6 | $R_{C_2H_6} = k_2 \exp(E_2/RT)C_{H_2}^1$ | 2.289E10 | 160 |
| 3 | 7H2+3CO→ 3H2O+C3H8 | $R_{C_3H_8} = k_3 \exp(E_3/RT)C_{H_2}^1$ | 4.579E10 | 160 |
| 4 | 9H2+4CO→ 4H2O+C4H10 | $R_{C_4H_{10}} = k_6 \exp(E_6/RT)C_{H_2}^1$ | 2.289E10 | 160 |
| 5 | H2O+CO→ H2+CO2 | $R_{CO_2} = k_4 e^{-E_4/RT} C_{H_2O} C_{CO}$ | 7.649E01 | 100 |
| 6 | 29H2+14CO→ 14H2O+ C14H30 | $R_{FT} = \dfrac{k_6 e^{-E_6/RT} C_{H_2} C_{CO}}{\left[1 + k_a e^{-E_a/RT} C_{CO}\right]^2}$ | 3.302E06 | 100 |

FIG. 25

INTEGRATED MICROCHANNEL SYNTHESIS AND SEPARATION

CROSS-REFERENCE TO RELATED APPLICATIONS

The present application claims priority to United States nonprovisional patent application entitled "INTEGRATED MICROCHANNEL SYNTHESIS AND SEPARATION", U.S. Ser. No. 11/516,027 filed on Sep. 5, 2006, the entire content of which is hereby incorporated by reference.

RELATED ART

Field of the Invention

The present invention is directed to equipment, and processes utilizing such equipment, for carrying out microchannel unit operations and, more specifically, to multiple microchannel unit operations integrated into a single device or assembly.

INTRODUCTION TO THE INVENTION

The present invention is directed to equipment, and processes utilizing such equipment, for carrying out microchannel unit operations and, more specifically, to multiple microchannel unit operations integrated into a single device or assembly. The present invention includes synthesis chemical reactors integral with heat exchangers and optionally phase separators or other means of chemical separation. Still further, the integration of microchannel technology into multiple unit operations allows for greater plant flowsheet optimization and consolidation to reduce interconnecting piping, pressure losses, associated costs and size reduction. Moreover, the exemplary microchannel equipment may be utilized in on-shore and off-shore applications, including but not limited to where space is limited and conversion of gaseous materials to liquids is preferred for storage, handling and transportation considerations.

The present invention also includes microchannel based equipment and associated processes for carrying out various exemplary chemical reactions and separation processes including, without limitation, microchannel steam methane reforming (SMR). Utilization of microchannel based equipment results in various advantages, depending upon the process or processes carried out. For example, in an SMR process, utilization of microchannel based equipment can be operated with a lower steam to carbon ratio, which results in substantially less water requirements than traditional SMR units. This can be particularly advantageous in environments where ready supply of clean water requires expensive treatment, such as desalination. In addition, the use of a steam reformer to produce synthesis gas eliminates the need for oxygen, as required for partial oxidation or autothermal reforming. Moreover, microchannel process technology has many advantages over conventional reforming, methanol synthesis, and distillation technologies. These advantages will allow smaller, less expensive equipment to produce commercially significant quantities of methanol in on-shore and off-shore environments.

It is a first aspect of the present invention to provide a process for the formation of methanol, the process comprising the steps of: (a) inputting a feed stream comprising carbon containing molecules and hydrogen containing molecules to a microchannel reactor; (b) reacting a portion of the carbon containing molecules with the hydrogen containing molecules within the microchannel reactor to form methanol molecules flowing in a process stream; (c) removing at least some of the formed methanol molecules from the process stream; (d) reacting a further portion the carbon containing molecules with the hydrogen containing molecules to form methanol molecules flowing in the process stream, where greater than ninety percent of the carbon containing molecules have been reacted to form methanol.

In a more detailed embodiment of the first aspect, the method further comprises: (a2) changing at least one of temperature and pressure of the feed steam prior to step (b). In yet another more detailed embodiment, the method further comprises: (b2) changing at least one of temperature and pressure of the feed steam prior to step (c). In a further detailed embodiment, the method further comprises (b2) recouping at least some of the energy generated within the microchannel reactor by thermal communication with a lower energy fluid stream within the microchannel reactor. In still a further detailed embodiment, the method further comprises: (c2) changing at least one of temperature and pressure of the feed steam prior to step (d). In a more detailed embodiment, the method further comprises: (b2) changing at least one of temperature and pressure of the process steam prior to step (c); and (c2) changing at least one of temperature and pressure of the process stream after step (c) and before step (d), where step (b2) is carried out in a first heat exchanger integrated with the microchannel reactor, and where step (c2) is carried out in a second heat exchanger integrated with the microchannel reactor. In a more detailed embodiment, the method further comprises: (e) delivering a heat transfer fluid medium into thermal communication with the process stream flowing through at least one of the first heat exchanger and the second heat exchanger. In another more detailed embodiment, the method further comprises: (b2) changing at least one of temperature and pressure of the process steam prior to step (c); and (c2) changing at least one of temperature and pressure of the process stream after step (c) and before step (d), where step (b2) and step (c2) are carried out in a heat exchanger integrated with the microchannel reactor. In yet another more detailed embodiment, the method further comprises: (b2) directing the process stream into a microchannel separation unit operation, where step (b) includes distributing the feed stream among a plurality of microchannels to comprise a plurality of sub-process streams, and step (b2) includes the step of maintaining separability of the sub-process streams upon entry into the microchannel separation unit operation. In still another more detailed embodiment, the method further comprising: (a2) distributing the feed stream among a plurality of microchannels of the microchannel reactor that are operative to form a plurality of sub-process streams directly conveying the feed steam to at least one unit operation.

In yet another more detailed embodiment of the first aspect, the unit operation includes at least one of a chemical reactor, a chemical separator, a heat exchanger, a compressor, an expander, a vaporizer, a condenser, a phase separator, and a mixer. In still another more detailed embodiment, the microchannel reactor of step (a) includes two separate microchannel reactors, the feed stream of step (a) is distributed among the two separate microchannel reactors, the process stream of step (b) comprises each outlet process stream from the two separate microchannel reactors, a first outlet process stream from one of the two separate microchannel reactors is fed to a downstream heat exchanger, a second outlet process stream from the other of the two separate microchannel reactors is fed to the downstream heat exchanger, in step (c) the first outlet process stream is cooled to a lower temperature within the heat exchanger to liquefy at least one of the methanol molecules and forming a gaseous phase process stream lean in methanol molecules, the second outlet process stream is in thermal communication with the gaseous phase process stream and is operative to elevate the temperature of the gaseous phase process stream. In a further detailed embodiment, the method further comprises: (b2) performing a heat exchange operation between the process stream and a cooling fluid stream flowing through the microchannel reactor, where the process stream is not in fluid communication with the cooling fluid stream, where step (b2) includes distributing the process stream among a plurality of microchannels to comprise a plurality of sub-process streams, and step (b2) includes distributing the cooling fluid stream among a plurality of cooling microchannels of the microchannel reactor to comprise a plurality of sub-cooling fluid streams. In still a further detailed embodiment, the method further comprises: (b2) directing the process stream into a microchannel separation unit operation; and (b3) performing a heat exchange operation between the process stream and a cooling fluid stream flowing through the microchannel separation unit operation, where the process stream is not in fluid communication with the cooling fluid stream, step (b2) includes distributing the process stream among a plurality of microchannels to comprise a plurality of sub-process streams, step (b2) includes distributing the cooling fluid stream into thermal communication with the process stream, and step (b2) includes the step of maintaining separability of the sub-process streams upon entry into the microchannel separation unit operation.

In a more detailed embodiment of the first aspect, where step (b2) includes distributing the cooling fluid stream among a plurality of cooling microchannels of the microchannel separation unit operation that are in thermal communication with the process stream. In yet another more detailed embodiment, the feed to the microchannel reactor does not include a recycle stream. In a further detailed embodiment, the microchannel reactor includes discrete stages. In still a further detailed embodiment, at least one of the discrete stages does not include a recycle stream. In a more detailed embodiment, a first stage of the discrete stages of the microchannel reactor includes a catalyst, and step (c) includes introducing the feed stream to the catalyst of the first stage for contact times between about 1000 milliseconds to about 10 milliseconds, where contact time is defined by the open volume of the reactor chamber that houses the catalyst divided by the standard state feed flowrate. In a more detailed embodiment, step (d) is carried out within the microchannel reactor. In another more detailed embodiment, a percentage of methanol molecules removed in step (c) from those formed in a first stage of the discrete stages is between about fifty percent to about ninety-five percent. In yet another more detailed embodiment, the method further comprises: (f) repeating step (c) and step (d) to achieve greater than ninety percent conversion of the carbon containing molecules to form methanol, where the microchannel reactor includes discrete stages, step (d) is first carried out in a second stage of the microchannel reactor, repeated step (d) is carried out in a third stage of the microchannel reactor, downstream from the second stage of the microchannel reactor, and an operating temperature of the second stage is higher than an operating temperature of the third stage. In still another more detailed embodiment, step (a) through step (d) are carried out within a single microchannel assembly.

In yet another more detailed embodiment of the first aspect, the process produces greater than 30 kilograms of methanol molecules per day. In still another more detailed embodiment, the microchannel reactor has a displaced volume of less than 200 meters cubed per thousand metric tons of methanol per day. In a further detailed embodiment, the microchannel reactor has a displaced volume of less than 80 meters cubed per thousand metric tons of methanol per day. In still a further detailed embodiment, step (a) and step (b) are carried out within a containment vessel. In a more detailed embodiment, the feed stream includes products from a syngas generation process carried out within at least one of a steam reformer, a partial oxidation reactor, and a gasifier, and a separator interposes the syngas generation process and the microchannel reactor, the separator being operative to remove water from the stream exiting from the syngas generation process. In a more detailed embodiment, the syngas generation process is a natural gas steam reformer and includes microchannels, and the natural gas steam reforming process is carried out within the microchannels of the steam reformer. In another more detailed embodiment, the water removed by the separator is utilized to cool the microchannel reactor. In yet another more detailed embodiment, the separator is a microchannel separator, at least one output stream from the microchannel separator comprises the feed stream to the microchannel reactor, and a compressor is downstream from the microchannel separator to compress the feed stream before delivery to the microchannel reactor.

In yet another more detailed embodiment of the first aspect, the feed stream includes products from a natural gas steam reforming process carried out within a steam reformer, and a heat exchanger interposes the steam reformer and the microchannel reactor to remove energy from the products exiting the microchannel reactor. In still another more detailed embodiment. In a further detailed embodiment, the heat exchanger is a microchannel heat exchanger, at least one output stream from the microchannel heat exchanger comprises the feed stream, and a compressor is downstream from the microchannel heat exchanger to compress the feed stream before delivery to the microchannel reactor. In a more detailed embodiment, step (c) includes utilizing at least one of a microchannel distillation unit, a capillary separation unit, and a microchannel membrane separation unit to remove at least some of the formed methanol from the process stream. In a more detailed embodiment, the carbon containing molecules and hydrogen containing molecules of the feed stream comprise syngas from at least one of a natural gas steam reforming process, a liquid-to-gassification process, and a solid-to-gasification process.

It is a second aspect of the present invention to provide a process for carrying out at least two unit operations in series, the process comprising the step of: (a) directing a feed stream into an integrated assembly which comprises a first microchannel unit operation upon at least one chemical of the feed stream to generate a distributed output stream that exits the first microchannel unit operation in a first set of discrete microchannels isolating flow through the discrete microchannels; (b) directing the distributed output stream of the first microchannel unit operation into a second microchannel unit operation as a distributed input stream, to continue isolating flow between the first set of discrete microchannels, and conducting at least one operation upon at least one chemical of the input stream to generate a product stream that exits the second microchannel unit operation, where the first microchannel unit operation and the second unit operation share a housing.

In another more detailed embodiment of the second aspect, the operation conducted upon at least one chemical of the input stream includes at least one of a chemical reactor, a chemical separator, a heat exchanger, a compressor, an expander, a vaporizer, a condenser, a phase separator, and a mixer. In still another more detailed embodiment, the first microchannel unit operation includes two parallel unit operations, comprising a first parallel unit operation and a second parallel unit operation, the feed stream is distributed among the two parallel unit operations, the distributed output stream includes separate distributed output substreams from each of the two parallel unit operations, the second microchannel operation comprises a heat exchanger, a first distributed output substream from the first parallel unit operation is fed to the heat exchanger, a second distributed output substream from the second parallel unit operation is fed to the heat exchanger, the first distributed output substream is cooled to a lower temperature within the heat exchanger to liquefy a chemical of the first distributed output substream and form a gaseous phase process stream lean in the chemical, and the second distributed output substream is in thermal communication with the gaseous phase process stream and is operative to elevate the temperature of the gaseous phase process stream. In a further detailed embodiment, the feed stream flowing through the first microchannel unit operation is split among a plurality of microchannels having a plurality of microchannel outlets from the first microchannel unit operation, the input stream flowing through the second microchannel unit operation is split among a plurality of microchannels having a plurality of microchannel inlets that receive the input stream, and an interface between first microchannel unit operation and the second microchannel unit operation connects the plurality of microchannel outlets of the first microchannel unit operation to the plurality of microchannel inlets of the second microchannel unit operation while conserving the separability of the streams flowing through the microchannels at the interface. In still a further detailed embodiment, at least one of the first microchannel unit operation and the second microchannel unit operation is fabricated using from a laminate structure. In a more detailed embodiment, the first microchannel unit operation conducts a chemical reaction, the second microchannel unit operation conducts a phase separation operation, and the chemical reaction conducted in the first microchannel unit operation is equilibrium limited. In a more detailed embodiment, the chemical reaction is at least one of methanol synthesis, ammonia synthesis, Fischer-Tropsch, acetylation, aldol condensation, alkylation, amination, dehydration, esterification, etherification, hydrolysis, isomerization, oligomerization, and transesterification.

It is a third aspect of the present invention to provide a process for the formation of methanol, the process comprising the steps of (a) inputting a first feed stream comprising carbon containing molecules and hydrogen containing molecules to a first microchannel reactor; (b) inputting a second feed stream comprising carbon containing molecules and hydrogen containing molecules to a second microchannel reactor, where the second microchannel reactor is in parallel with the first microchannel reactor; (c) reacting the carbon containing molecules with the hydrogen containing molecules in the presence of a catalyst housed within the first microchannel reactor to form methanol molecules flowing in a first process stream; (d) reacting the carbon containing molecules with the hydrogen containing molecules in the presence of a catalyst housed within the second microchannel reactor to form methanol molecules flowing in a second process stream; (e) directing the first process stream to a downstream heat exchanger; (0 directing the second process stream to a downstream heat exchanger; (g) cooling the first process stream within the downstream heat exchanger to condense at least one chemical comprising the first process stream; (h) extracting the chemical from the first process stream to form a cooled gaseous process stream; (i) directing the second process stream into thermal communication with the cooled gaseous process stream to increase the temperature and form an elevated temperature gaseous process stream having carbon containing molecules and the hydrogen containing molecules; (j) inputting elevated temperature gaseous process stream to a downstream microchannel reactor; and (k) reacting the carbon containing molecules with the hydrogen containing molecules in the presence of a catalyst housed within downstream microchannel reactor to form methanol molecules flowing in a downstream process stream.

It is a fourth aspect of the present invention to provide a process for the formation of methanol, the process comprising the steps of: (a) inputting a first feed stream comprising reactants to a first microchannel reactor; (b) inputting a second feed stream comprising reactants to a second microchannel reactor, where the second microchannel reactor is in parallel with the first microchannel reactor; (c) reacting at least some of the reactants in the presence of a catalyst housed within the first microchannel reactor to form product flowing in a first process stream; (d) reacting at least some of the reactants in the presence of a catalyst housed within the second microchannel reactor to form product flowing in a second process stream; (e) directing the first process stream to a downstream heat exchanger; (f) directing the second process stream to a downstream heat exchanger; (g) cooling the first process stream within the downstream heat exchanger to condense at least one chemical comprising the first process stream; (h) extracting the chemical from the first process stream to form a cooled gaseous process stream; (i) directing the second process stream into thermal communication with the cooled gaseous process stream to increase the temperature and form an elevated temperature gaseous process stream including remaining reactants; (j) inputting elevated temperature gaseous process stream to a downstream microchannel reactor; (k) reacting at least some of the remaining reactants in the presence of a catalyst housed within a downstream microchannel reactor to form product flowing in a downstream process stream.

In another more detailed embodiment of the fourth aspect, the feed stream to the microchannel reactor does not include a recycle stream. In still another more detailed embodiment, at least one of the first microchannel reactor and the second microchannel reactor includes discrete stages. In a further detailed embodiment, the feed stream flowing through the first microchannel reactor contacts the catalyst in step (c) between about 1000 milliseconds to about 10 milliseconds contact time, and the feed stream flowing through the second microchannel reactor contacts the catalyst in step (d) between about 1000 milliseconds to about 10 milliseconds. In still a further detailed embodiment, the method further comprises: (l) removing at least a portion of the product from the first process stream subsequent to egress of the product from the first microchannel reactor; and (m) removing at least a portion of the product from the second process stream subsequent to egress of the product from the second microchannel reactor. In a more detailed embodiment, step (l) is at least partially carried out within a distillation unit operation, at least one output stream from the distillation unit operation is a product rich stream, and at least a second output stream from the distillation unit operation is a product lean stream. In a more detailed embodiment, at least step (c) and step (d) are carried out within a containment vessel.

In yet another more detailed embodiment of the fourth aspect, the method further comprises: (I) removing at least a portion of the product from the first process stream subsequent to egress of the product from the first microchannel reactor; and (m) delivering a fuel stream to a stream reformer unit operation to generate energy necessary to carry out an endothermic steam reformation reaction on a hydrocarbon rich stream entering the steam reformer, where step (l) is at least partially carried out in a separator that interposes the steam reformer and the first microchannel reactor, the separator being operative to remove at least one component from a fuel rich stream exiting from the steam reformer unit operation, resulting in the fuel stream delivered to the steam reformer unit operation. In still another more detailed embodiment, the at least one component includes water, and the water removed by the separator is utilized as a cooling fluid flowing through the downstream heat exchanger of the first microchannel reactor. In a further detailed embodiment, the first feed stream is supplied by a natural gas steam reforming process carried out within a steam reformer, and a heat exchanger interposes the steam reformer and the first microchannel reactor to remove energy from the first feed stream prior to entering the first microchannel reactor. In still a further detailed embodiment, the chemical of step (h) includes methanol, and step (h) includes utilization of at least one of a microchannel distillation unit, a capillary separation unit, and a microchannel membrane separation unit to remove at least some of the chemical from the first process stream. In a more detailed embodiment, the reactants of the first feed stream comprise syngas from a natural gas stream reforming process.

It is a fifth aspect of the present invention to provide a process for the formation of methanol, the process comprising: (a) inputting a hydrocarbon feed stream to a steam reformation reactor that houses a first catalyst; (b) bringing steam into communication with the hydrocarbon feed stream; (c) reacting hydrocarbons of the hydrocarbon feed stream with steam in the presence of a catalyst to form a syngas stream comprising carbon dioxide, carbon monoxide and hydrogen; (d) inputting the syngas stream to a staged microchannel methanol synthesis reactor that houses a second catalyst; (e) reacting the syngas in the presence of the second catalyst within the microchannel synthesis reactor to form methanol molecules flowing in a reactant and product stream, where greater than ninety percent of the carbon containing molecules of the syngas, on a carbon basis, are converted into methanol molecules synthesized within the staged microchannel methanol synthesis reactor, where the staged microchannel reactor includes at least three stages, and methanol molecules are removed from the reactant and product stream between at least two of the three stages.

In another more detailed embodiment of the fifth aspect, at least two of the three stages are interposed by unit operation comprising at least one of a microchannel heat exchanger and a microchannel phase separator, and the unit operation receives an output stream from an immediately upstream stage, where the output stream microchannels flow directly into the microchannels of the unit operation. In still another more detailed embodiment, greater than fifty percent of the carbon containing molecules of the syngas, on a carbon basis, are converted into methanol molecules synthesized at the end of the first stage. In a further detailed embodiment, greater than seventy-five percent of the carbon containing molecules of the syngas, on a carbon basis, are converted into methanol molecules synthesized at the end of the second stage. In still a further detailed embodiment, the steam reformation reactor includes a microchannel steam reformation reactor.

It is a sixth aspect of the present invention to provide an integrated microchannel reactor and separator comprising: (a) a first network of microchannels housing a first catalyst to facilitate at least one of a molecular cracking reaction or a molecular synthesis reaction; (b) a second network of microchannels downstream from the first network of microchannels, the second network of microchannels include micropores operative to separate extract at least one of a liquid and a gas flowing through the second network of microchannels, where an interface between the first network of microchannels and the second network of microchannels involves a pressure drop change of less than fifty percent; (c) a third network of microchannels housing a second catalyst to facilitate at least one of a molecular cracking reaction or a molecular synthesis reaction, the first network of microchannels being downstream from the second network of microchannels, where an interface between the second network of microchannels and the third network of microchannels involves a pressure drop change of less than fifty percent; and (d) a fourth network of microchannels downstream from the third network of microchannels, the fourth network of microchannels include micropores operative to separate extract at least one of a liquid and a gas flowing through the fourth network of microchannels, where an interface between the third network of microchannels and the fourth network of microchannels involves a pressure drop change of less than fifty percent.

In another more detailed embodiment of the sixth aspect, an interface between the second network of microchannels and the third network of microchannels involves a pressure drop change of less than fifty percent. In still another more detailed embodiment, an interface between the third network of microchannels and the fourth network of microchannels involves a pressure drop change of less than fifty percent. In a further detailed embodiment, the first catalyst at least one of lines or packs at least a portion of the first network of microchannels, and the second catalyst at least one of lines or packs at least a portion of the third network of microchannels. In still a further detailed embodiment, the pressure drop change of less than fifty percent is at least partially a result of avoiding consolidation of the microchannels comprising the first microchannel network approximate the interface between the first and second network of microchannels, and fewer than seventy-five percent of the microchannels of the first microchannel network are consolidated approximate the interface between the first and second network of microchannels. In a more detailed embodiment, the pressure drop change of less than fifty percent between the second and third microchannel networks is at least partially a result of avoiding consolidation of the microchannels comprising the second microchannel network approximate the interface between the second and third network of microchannels, and fewer than seventy-five percent of the microchannels of the second microchannel network are consolidated approximate the interface between the second and third network of microchannels. In a more detailed embodiment, the pressure drop change of less than fifty percent between the third and fourth microchannel networks is at least partially a result of avoiding consolidation of the microchannels comprising the third microchannel network approximate the interface between the third and fourth network of microchannels, and fewer than seventy-five percent of the microchannels of the third microchannel network are consolidated approximate the interface between the third and fourth network of microchannels.

BRIEF DESCRIPTION OF THE DRAWINGS

FIG. 25 is an exemplary set of six reactions utilized to model the FT reaction system;

DETAILED DESCRIPTION

The exemplary embodiments of the present invention are described and illustrated below to encompass equipment, and processes utilizing such equipment, for carrying out microchannel unit operations. As used herein, the term microchannel refers to any conduit having at least one dimension (height, length, or width) (wall-to-wall, not counting catalyst) of 1 cm or less, including 2 mm or less (in some embodiments about 1.0 mm or less) and greater than 100 nm (preferably greater than 1 μm), and in some embodiments 50 to 500 μm. Microchannels are also defined by the presence of at least one inlet that is distinct from at least one outlet. Microchannels are not merely channels through zeolites or mesoporous materials. The length of a microchannel corresponds to the direction of flow through the microchannel. Microchannel height and width are substantially perpendicular to the direction of flow of through the channel. In the case of a laminated device where a microchannel has two major surfaces (for example, surfaces formed by stacked and bonded sheets), the height is the distance from major surface to major surface and width is perpendicular to height. Of course, it will be apparent to those of ordinary skill in the art that the exemplary embodiments discussed below are illustrative in nature and may be reconfigured without departing from the scope and spirit of the present invention. However, for clarity and precision, the exemplary embodiments as discussed below may include optional steps, methods, and features that one of ordinary skill should recognize as not being a requisite to fall within the scope of the present invention.

For purposes of this disclosure, an "assembly" is a containment vessel that contains one or more microchannel unit operations that operate in parallel (if more than 1 unit). Fluid flow is to the units and discharged by way of the effluent streams of each unit.

For purposes of the disclosure, a "unit operation" includes equipment operative to conduct one of more of the following: chemical reactions; chemical separations (including absorption, distillation, adsorbing, extraction); heat exchange; compressing; expanding; vaporizing; condensing; phase separation; and mixing.

For purposes of the disclosure, a "waveform" is a contiguous piece of thermally conductive material that is transformed from a planar object to a 3-dimensional object that at least partially defines one or more microchannels. The waveform may have a gap between the waves that is in the microchannel dimension or may be larger. In exemplary form, this gap may be in the microchannel dimension because then heat is easily transferred to the long direction in the wave that separates the heat transfer channels before conducting down the more conductive wave form to the heat transfer channels. The waveform may be made of copper, aluminum, metals, oxides, or other materials with a thermal conductivity greater than 1 W/m-K.

Figure 1:
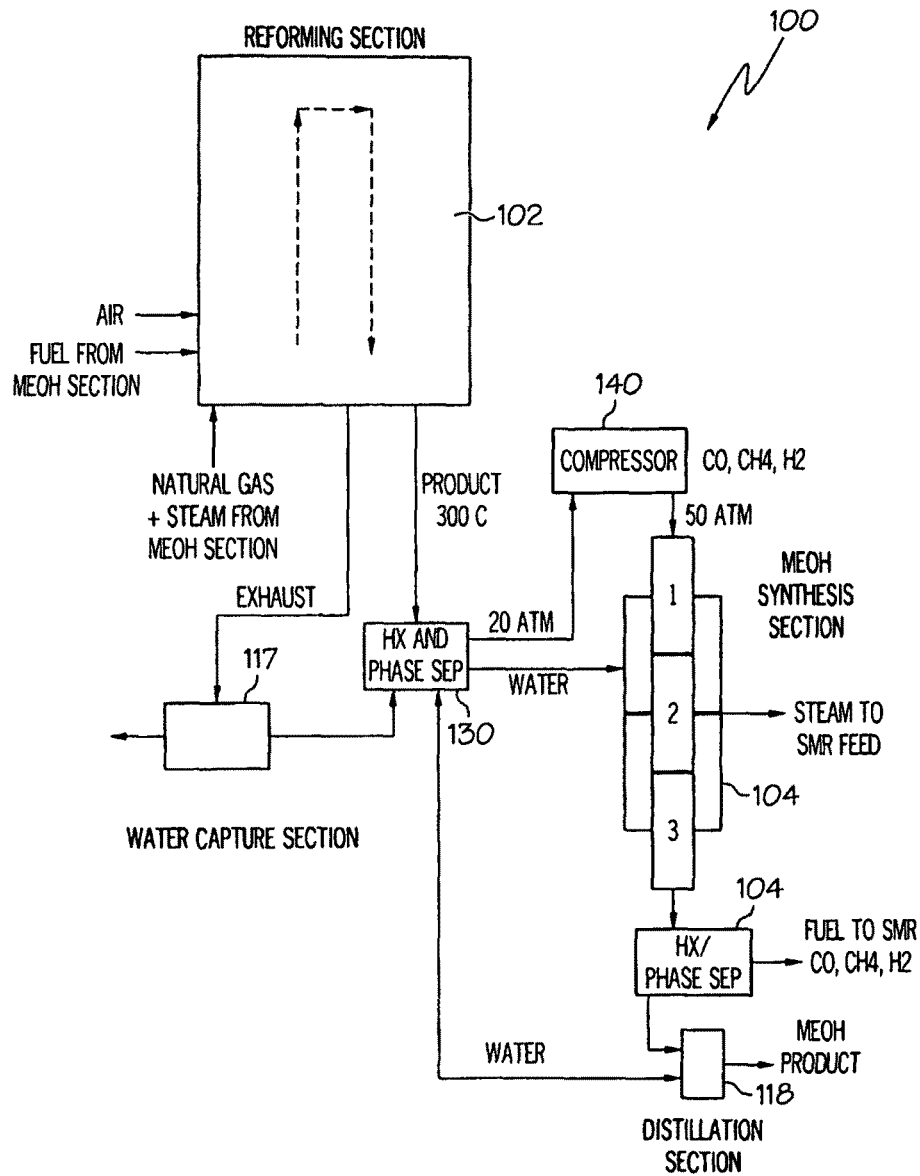
FIG. 1 is an exemplary schematic diagram of an exemplary plant layout in accordance with the present invention.

Referencing FIG. 1, a first exemplary embodiment comprises a compact microchannel plant 100, suitable for installation in an on-shore or off-shore application, that includes a microchannel steam reformer 102 and a downstream methanol synthesis reactor 104. The exemplary microchannel plant 100 may include the following salient features which make it particularly advantageous for off-shore applications: 1) its compact hardware with a reduced number of discrete components to minimize deck space; 2) short distillation towers to accommodate for vessel sway; 3) minimal requirements for freshwater; and 4) competitive carbon efficiency and overall economics. It is to be understood, however, that embodiments having less than all of these features may nonetheless fall within the scope of the present invention.

An exemplary application where the microchannel plant 100 is particularly suited is off-shore conversion of natural gas to liquid methanol. In this application, natural gas is converted to synthesis gas (hereafter referred to as "syngas" which predominantly comprises carbon dioxide, carbon monoxide and hydrogen gases, as well as water) within the microchannel steam reformer 102 using a process commonly known as steam reformation. However, it is also within the scope of the invention use processes to form syngas including, without limitation, gasifying solids such as coal, biomass, industrial wastes, municipal solid waste, sewage sludge(s), petroleum coke, tar sands or bitumen, or gasifying liquids such as naphtha, residual oil(s), LNG, LPG. Nevertheless, for purposes of brevity, the exemplary embodiments for the syngas production have been described as including a steam reformation process. Steam reformation is an endothermic reaction where natural gas (methane, ethane, propane, etc.) is mixed with steam and reacted at high temperatures (700-1000 C) in the presence of a catalyst facilitating chemical reactions between the natural gas molecules and water molecules to produce syngas. Designs of exemplary microchannel steam reformer reactors and variations thereof have been described previously in publications US2004/0031592 by Mathias et al., US2004/0033455 by Tonkovich et al., US2005/0087767 by Fitzgerald et al., and US2005/0175519 by Rogers et al., the disclosures of each of which are hereby incorporated to the instant disclosure by reference.

Outputs from the microchannel steam reformer 102 include a syngas stream and an exhaust stream from heat transfer microchannels in thermal communication with the microchannels carrying the syngas stream and precursor reactant stream. The exhaust stream comprises the products from an exothermic reaction carried out within the heat transfer microchannels, such as combustion, that transfer energy to the microchannels carrying the syngas and any precursor reactants to supply sufficient activation energy to carry out the stream reforming reaction. It is to be understood, however, that in lieu of an exothermic reaction taking place within the heat transfer microchannels, it is within the scope of the invention to convey superheated fluids therethrough operative as a heat or energy source to drive the steam reformation reaction.

Where overall freshwater retention is an important consideration for plant 100 operation, such as in off-shore applications, a collection unit operation 117 receives the exhaust gas stream and is operative to remove at least some of the water from the exhaust stream and recycle the water to one or more unit operations (such as 102) throughout the plant 100. It is to be understood that collection of water from the exhaust effluent is optional, however, and reduces the total amount of freshwater needing to be obtained on a recurring basis, such as a desalination unit, for plant 100 operation. As will be discussed in more detail later, the fuel is supplied to the steam reformer 102 from an outlet stream of a distillation unit 118 downstream from the methanol synthesis reactor 104.

Figure 2:
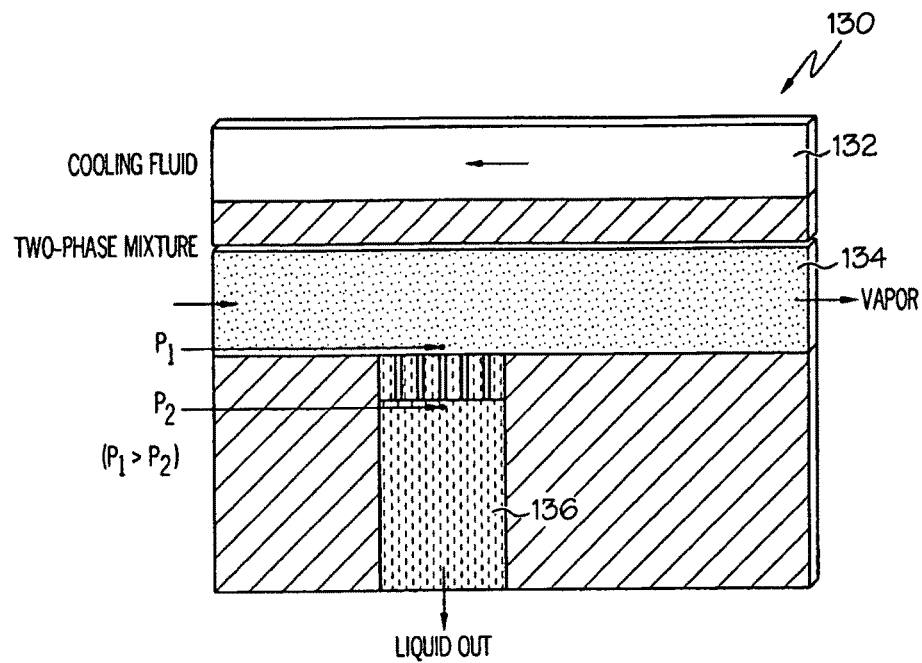
FIG. 2 is an exemplary isolated cross-sectional view of an exemplary heat exchanger and phase separator in accordance with the present invention.

Referencing FIGS. 1 and 2, a microchannel heat exchanger and phase separator 130 is downstream from the stream reformer 102 and includes three sets of microchannels 132, 134, 136. The first set of microchannels 132 carries a cooling fluid, for example, liquid water from a distillation unit 118, into thermal communication with the second set of microchannels 134 carrying the wet syngas product (two-phase). The enthalpy gradient between the cooling fluid and the wet syngas product is such that energy is transferred from the wet syngas product to the cooling fluid, resulting in condensation of the water component within the wet syngas product flowing through the second set of microchannels 134. The direction of flow of cooling fluid may be co-current, counter-current, or cross-flow with respect to the direction of flow of the two-phase wet syngas product. Condensed water from the second set of microchannels 134 is carried away using the third set of microchannels 136. The water flowing through the third set of microchannels 136 is fed to the methanol synthesis reactor 104 and operates within the reactor 104 as a heat transfer fluid. A downstream portion of the second set of microchannels 134 delivers the relatively dry syngas product at approximately 20 bar from the microchannel heat exchanger and phase separator 130 to the methanol synthesis reactor 104 or to an optional compressor 140. In this exemplary embodiment, the compressor 140 pressurizes the dry syngas product from approximately 20 bar to approximately 50 bar or higher for entry into the methanol synthesis reactor 104. It is to be understood, however, that the compressor 140 is not a required piece of equipment and may be omitted under certain operating conditions.

Synthesis of methanol is strongly equilibrium limited and occurs by reacting the dry syngas product, in the presence of a catalyst, to form methanol. This reaction is exothermic and is represented below as Equation set (1):

$$CO + 2\,H_2 \rightarrow CH_3OH;\ \text{Delta}\ H_{(300K)} = -90.77\ kJ/mol$$

$$CO_2 + 3\,H_2 \rightarrow CH_3OH + H_2O;\ \text{Delta}\ H_{(300K)} = -49.16\ kJ/mol \qquad (1)$$

(Reference: Uhlmann's, "Encyclopedia of Industrial Chemistry")

Figure 3:
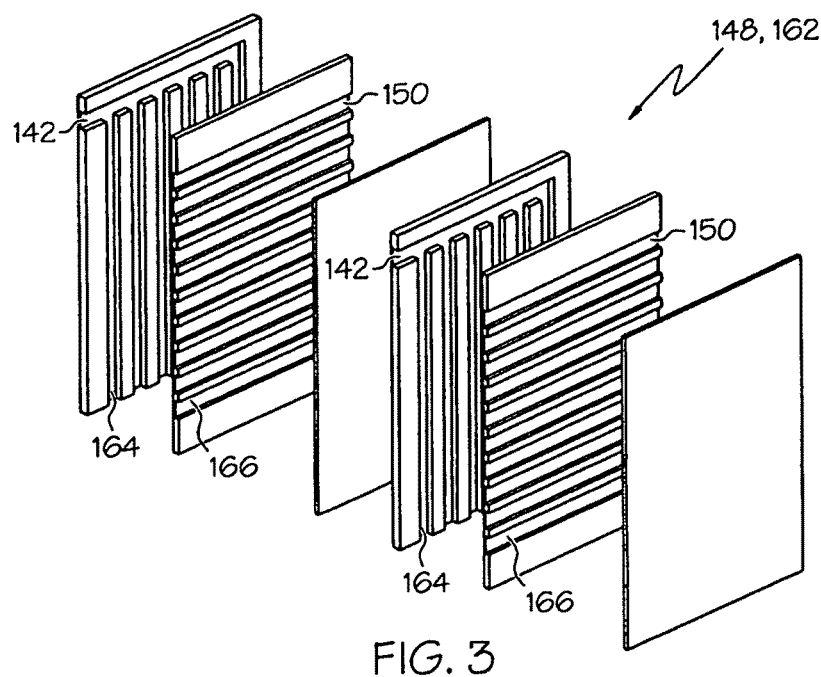
FIG. 3 is an exploded view of an exemplary heat exchanger and phase separator in accordance with the present invention.
Figure 4A:
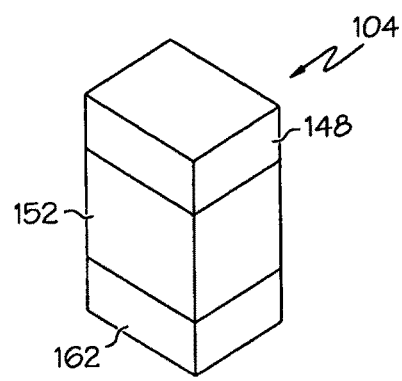
FIG. 4 is an exemplary exploded view of a unit operation made from laminates and useful for heat exchangers, chemical reactors, phase separations, other separations, fluid manifolding or distribution, mixing among others.
Figure 4B:
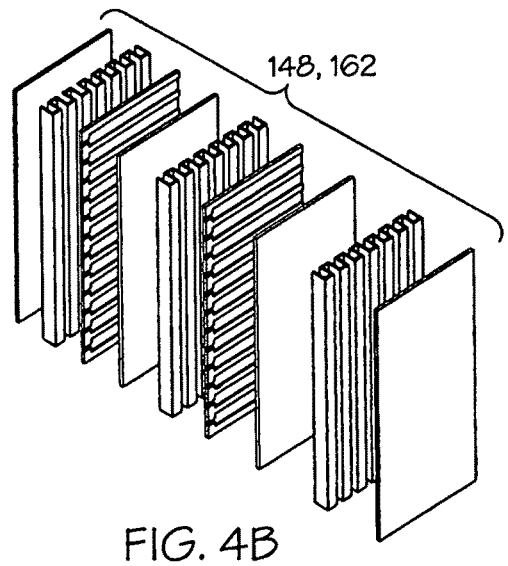
Figure 4C:
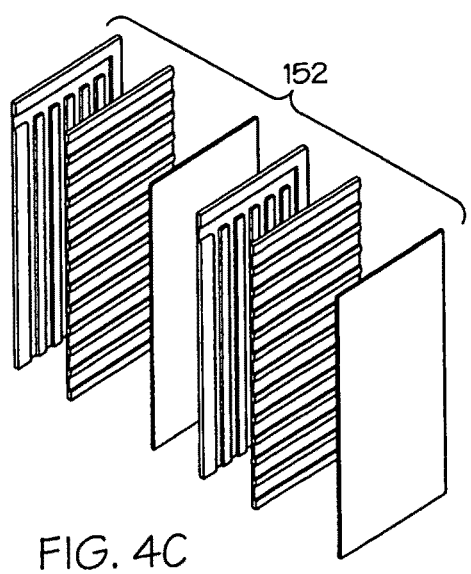

Referring to FIGS. 3 and 4, the methanol synthesis reactor 104 includes a first network of microchannels 142 within a preheating section 148 that receive the dry syngas product directly from the separator 130 or from the compressor 140, when optionally utilized. Distribution of the pressurized syngas product via the microchannel network 142 brings the syngas product into thermal communication with a heat transfer medium, such as steam, flowing through a second network of microchannels 150 of the preheating section 148 of the reactor 104. Dry syngas product flows through the microchannel network 142 of the preheating section 148 (see FIG. 4) and into reaction microchannels 154 without utilization of a prior art manifolds. As will be discussed in more detail later, the heat transfer medium may be supplied to the second network of microchannels 150 by a recycle stream within the methanol synthesis reactor 104 that forms or carries steam into thermal communication with at least a portion of the synthesis microchannels where methanol synthesis is occurring to carry away a portion of the exothermic energy generated as a result of methanol synthesis.

Figure 5A:
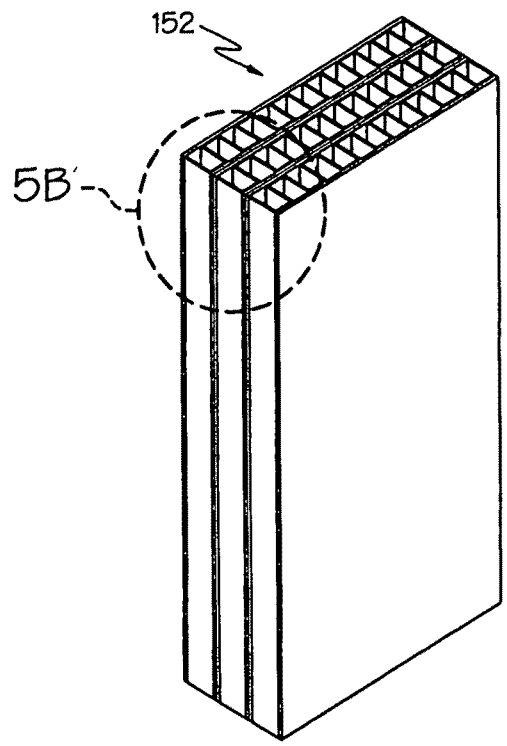
FIG. 5 is an elevated perspective view of an assembled unit operation made from a wave form and laminates and used in an exemplary methanol synthesis reactor with integral heat exchangers in accordance with the present invention.
Figure 5B:
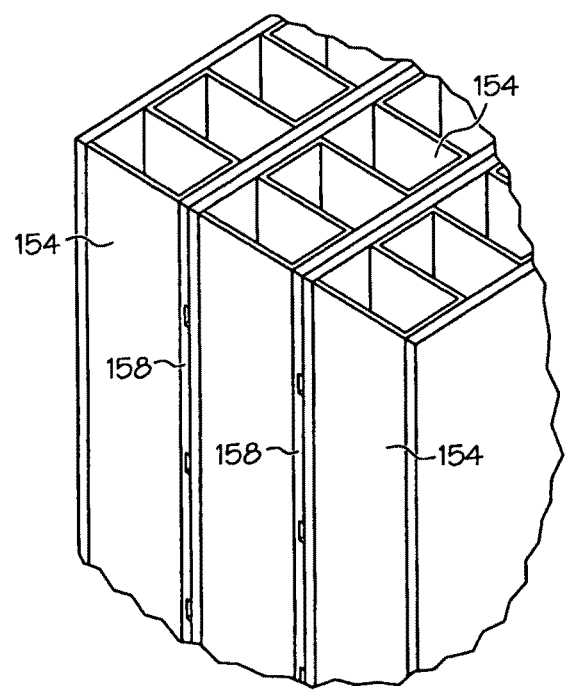
Figure 6:
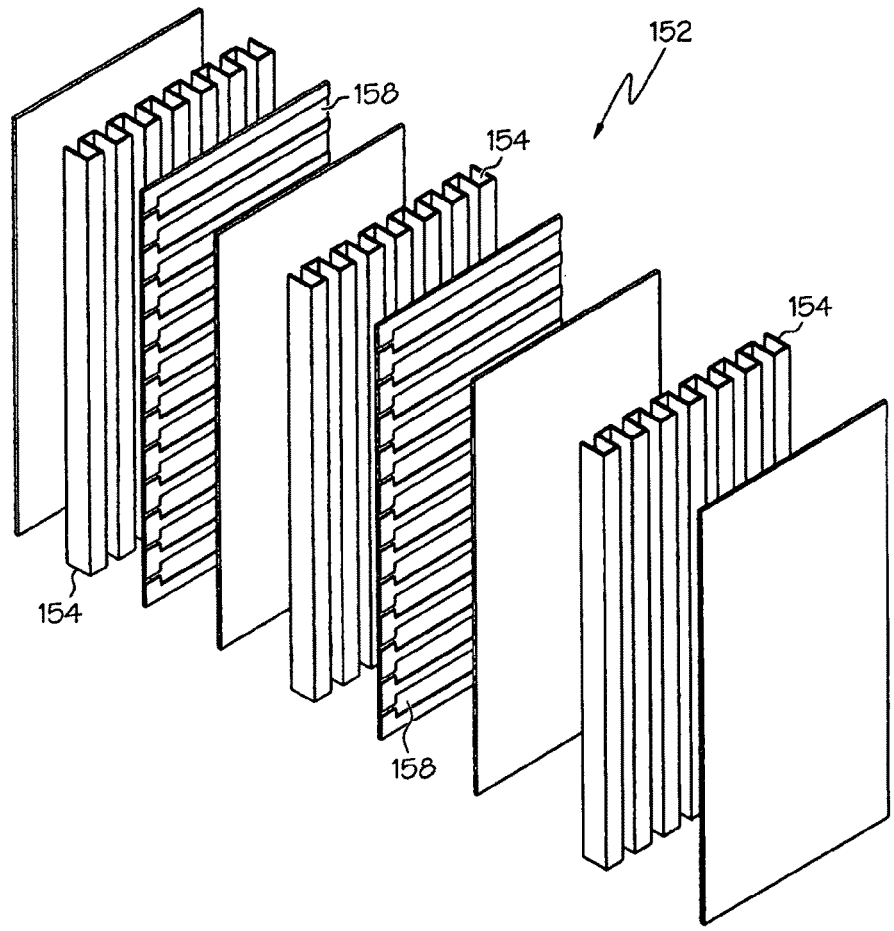
FIG. 6 is an exploded view of an exemplary unit operation made from a combination of a waveform channel and laminates and useful for a methanol synthesis reactor, an Fischer Tropsch reactor, an adsorber unit, an absorber, a heat exchanger or any other unit operation.

Referring to FIGS. 4-6, a first reactor stage 152 immediately follows the preheating section 148 and includes the reaction microchannels 154 introducing the syngas reactants to the synthesis catalyst. In this exemplary embodiment, the synthesis catalyst may be packed within the microchannels, lined along the walls of the microchannels, or otherwise configured within or grown within the microchannels of the first reactor stage 152. A grown catalyst includes one that includes a precursor in liquid solution or suspension that reacts, plates, crosslinks, or otherwise forms porous connections between the channel walls. The porosity may be macroporous, mesoporous, or microporous, or any combination of the three. A second set of microchannels 158 of the first reactor stage 152 are in thermal communication with the reaction microchannels 154 and convey a fluid heat transfer medium. In exemplary form, this medium is water that is partially boiled by the thermal energy generated in the exothermic synthesis of methanol to provide steam to various parts of the plant 100. The flow rate of the water through the microchannels 158 is precisely controlled to provide a reaction section that is essentially isothermal. By precisely controlling the pressure, temperature, reactions, and flowrates through the microchannels 154, the synthesis reactions may be maintained within a tight temperature tolerance, generally within ±40° C., or more preferably ±15° C., or even more preferably ±5° C.

The catalyst for the methanol synthesis or the FT reaction or others may be preferentially packed within the array of microchannels 154 and specifically packed between the waveform that directs heat from the packed catalyst to the heat transfer wall and then the cooling channels 158. In preferred embodiments the waveform is a high thermal conductivity material (>20 W/m-K, >50 W/m-K and more preferably >80 W/m-K and in one preferred embodiment is copper with a thermal conductivity greater than 300 W/m-K) such that the height of the waveform may be larger than the width of the microchannels therein (defined by the distance between each leg of the waveform). This novel configuration allows for a larger catalyst fraction within the reactor volume and thus in turn improves the reactor productivity per overall unit volume. The fraction of catalyst volume within the reactor volume is preferably greater than 30%, more preferably greater than 40%, and more preferably still greater than 50%. In one embodiment, the catalyst volume within the reactor exceeds 80%.

Referring to FIGS. 3 and 4, a first cooling stage 162 immediately follows the first reactor stage 152 and includes two sets of distributed microchannels 164, 166. The first set of microchannels 164 conveys the methanol and remaining syngas reactants from the first reactor stage 152, while the second set of microchannels 166 conveys a cooling fluid into thermal communication with the methanol and remaining syngas reactants. The direction of flow of cooling fluid may be co-current, counter-current, or cross-flow with respect to the direction of flow of the two-phase mixture.

The enthalpy difference between the synthesis stream (syngas reactants and methanol) flowing through the first set of microchannels 164 and the cooling fluid flowing through the second set of microchannels 166 is such that energy is transferred from the synthesis stream to the cooling fluid, thereby lowing the temperature of the synthesis stream. In this exemplary embodiment, the cooling fluid is water that at least partially vaporizes to produce a two-phase stream as a result of heat transfer from higher temperature methanol synthesis stream. The steam generated in the first set of microchannels 164 may be utilized as a steam input to the microchannel steam reformer 102.

Figure 7:
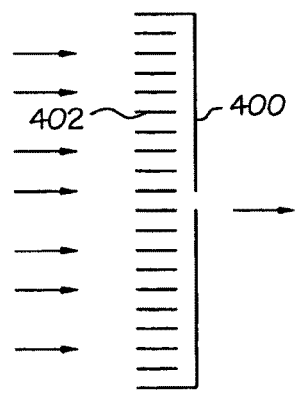
FIG. 7 is a prior art microchannel manifold where fluids combine from multiple parallel channels into a common outlet or a reduced number of outlets.
Figure 8A:
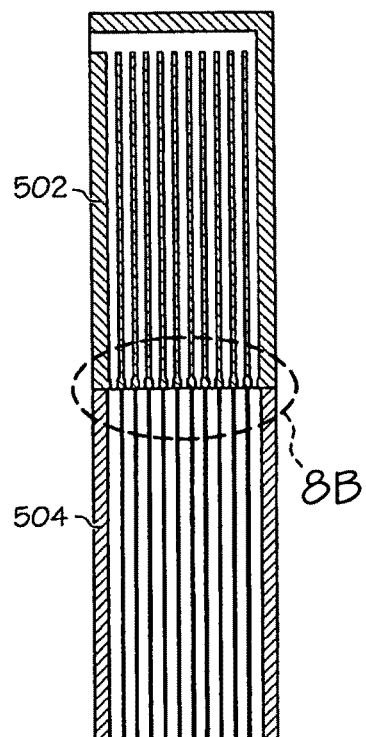
FIG. 8 is a cross-sectional view of a first exemplary interface between microchannel unit operations or sections of a microchannel unit operation.
Figure 8B:
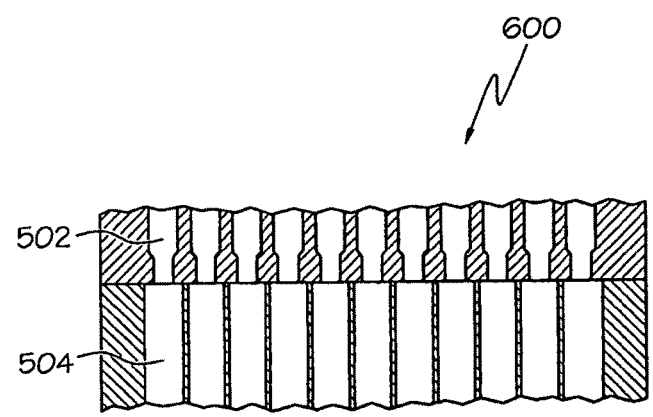

Referring to FIG. 7, conventional microchannel unit operations suffer from additional pressure drop as a result of manifolds 400 in series with the microchannels 402 distributed therein. These manifolds 400 were utilized in order establish fluid communication between a microchannel unit operation and another microchannel unit operation or a conventional unit operation. Manifolds 400 traditionally operate to consolidate numerous microchannels for exit from a microchannel unit operation or distribute a consolidated flow among a group of microchannels 402. This consolidation and distribution results in substantial pressure losses as fluid flows are impeded and eddy losses are increased. To overcome this undesirable pressure loss, the instant invention makes use of conservation of microchannels, which reduces the number of streams consolidated or resulting from distribution.

Referencing to FIG. 8-11, the present invention does not require use of manifolds between microchannel unit operations. In exemplary form, multiple output streams from a first unit operation or section of a unit operation 502 are fed to a similar number or equal number of inlet channels in a downstream unit operation or section of a downstream unit operation 504. This interface between unit operations or sections of the same unit operation is referred to as conservation of microchannels. Using conservation of microchannels, the flow does not substantially turn or move in an orthogonal direction to the flow path in the first unit operation or section as it enters a downstream unit operation or section. The resulting pressure loss in the connection between the first and downstream unit operation or section may be less than 10% of the pressure loss experienced using prior art manifold designs. Exemplary structures embodying conservation of microchannels between microchannel unit operations or unit operation sections are shown in FIGS. 8-11.

Figure 12:
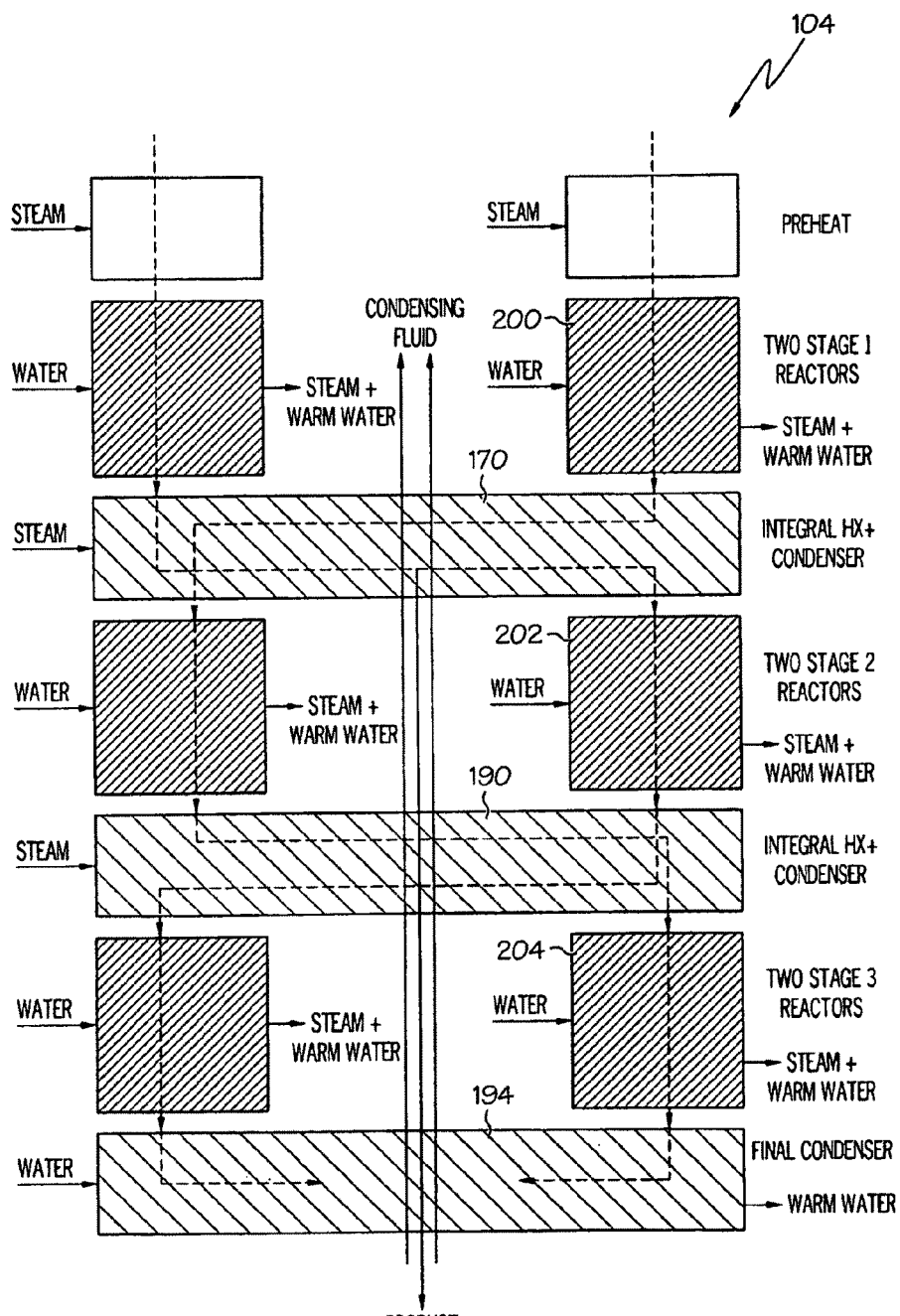
FIG. 12 is a schematic diagram of an exemplary integrated unit operation comprising microchannel heat exchangers, parallel reactors, and common condensers.

Referring to FIG. 12, the production of methanol is dependent upon the concentration of methanol within the system, the pressure of the system, the temperature of the system, and residence time the syngas reactants are in contact with the synthesis catalyst. An isopotential microchannel reactor 104, or parallel isopotential microchannel reactors 104, are exemplary ways to achieve a high single-pass conversion for an equilibrium limited reaction, such as methanol synthesis. If the temperature is dropped along the length of the reactor, the equilibrium potential for conversion is increased. In exemplary form, a three-stage series reactor 104 is constructed within a single reactor module, with the volume and temperatures being optimized based on the kinetics of a commercial methanol synthesis catalyst to minimize total reactor volume and contact time for the required inlet flowrate. Contact time is defined by the total reactor volume inclusive of a particulate form catalyst divided by the total volumetric flowrate of reactants at standard conditions. In the foregoing synthesis reactor 104, a contact time of 750 milliseconds gives a total CO conversion of 70.5% in the three-stage reactor.

The exemplary methanol synthesis microchannel reactor 104 incorporates cross flow of process fluids and heat exchange fluids. Three distinct reaction zones are designed down the length of the reactor 200, 202, 204. The first reaction zone 200 is 20% of the total reaction channel length, or 0.2 m of a 1-m length channel. The second reaction zone 202 extends 0.3 m of a 1-m length channel to the midpoint of the channel length. The third and final reaction zone 204 extends from the midpoint (0.5 m) to the channel end. The repeating unit geometry of the methanol synthesis microchannel reactor 104 is shown in FIG. 3. The design increases the ratio of the total catalyst volume per reactor to the total reactor volume to greater than 30%, and in some further exemplary embodiments greater than 70%. This high catalyst volume ratio offsets the longer reaction times for methanol synthesis as compared to steam methane reforming and generates a modest number of reactor assemblies. Based on these design dimensions, a total of 9 assemblies are required for 500 metric tons of methanol per day. Each methanol synthesis assembly is 1 m (wide)×1.2 m (high) by 3.9 m long—identical to the size of the steam methane reformer assembly. The resulting stack height of three assemblies is less than 7 m.

Figure 13:
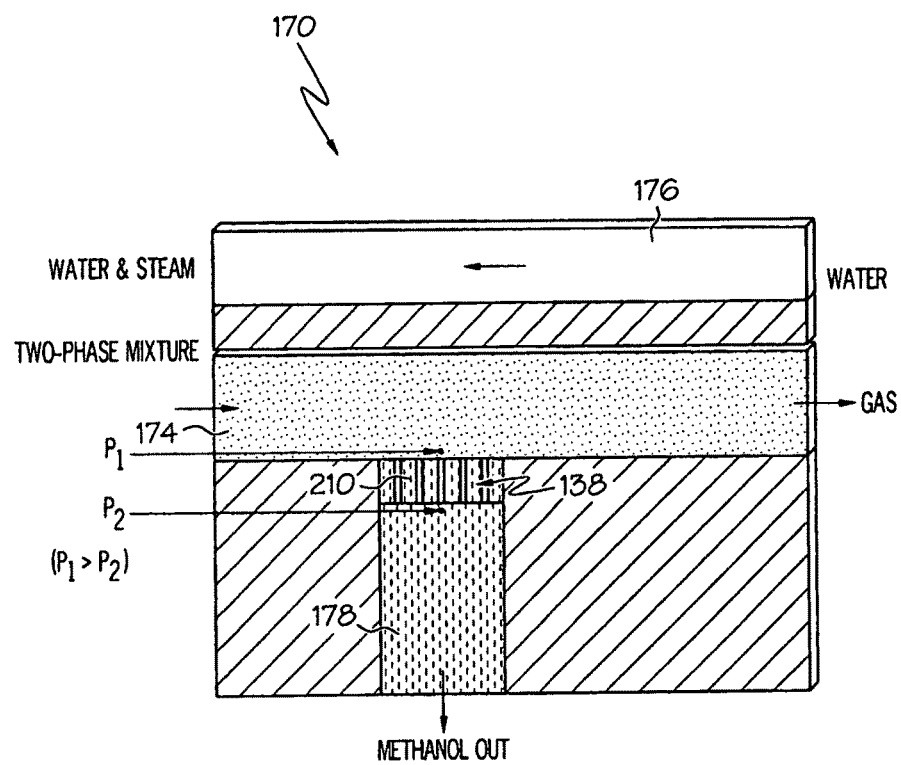
FIG. 13 is an exemplary isolated cross-sectional view of a second exemplary heat exchanger and phase separator in accordance with the present invention.

Referencing FIGS. 4, 12 and 13, higher concentrations of methanol within the reaction microchannels 154 housing the catalyst (not shown) decrease the frequency of reactions converting syngas to methanol because the reaction is equilibrium limited, thereby lowering the overall conversion of syngas products to methanol on a carbon conversion basis. In this manner, it is advantageous to reduce the concentration of methanol within the syngas stream. An integral microchannel heat exchanger and condenser 170 immediately follows the first cooling stage 162 and includes three sets of microchannels 174, 176, 178. The first set of microchannels 174 is downstream from the cooling microchannels 164 and conveys a decreased temperature synthesis stream into thermal communication with a cooling fluid flowing through the second set of microchannels 176 to lower the temperature of the methanol product below its boiling temperature. In this exemplary condenser 170, the cooling fluid is liquid water. This results in two-phase synthesis stream comprising methanol and unreacted syngas, as well as some by-product water. The first set of microchannels 174 convey the two-phase stream into communication with a capillary exclusion section 138.

Referring to FIG. 13, liquid capture (whether water or methanol) in the microchannel plant 100 is based on the principle of capillary exclusion. An exemplary capillary exclusion section 138 includes with a material with small pores 210 that bridges otherwise adjacent microchannels 174, 178. The pressure at P1 on one side of the small pores 210 is greater than P2 on the opposing side of the pores. Thus, when liquid comes in contact with the pores 210, the capillary pressure is greater than the breakthrough pressure of the gases, thereby forcing the liquid through the pores 210 and into the outlet microchannels 178. For circular pores, this relationship is show by Equation 2 below:

$$P_1 \le P_2 + \frac{2\sigma}{r} \qquad (2)$$

where: $\sigma$=surface tension between the gas and liquid phases
$r$=the radius of a single pore Pores of any shape may be used, which may require Equation (2) to be modified to an equivalent expression using hydraulic radius. Nevertheless, condensed methanol in the third set of microchannels 178 is carried away from the capillary exclusion section 138 and conveyed to the methanol distillation unit 118.

Figure 14:
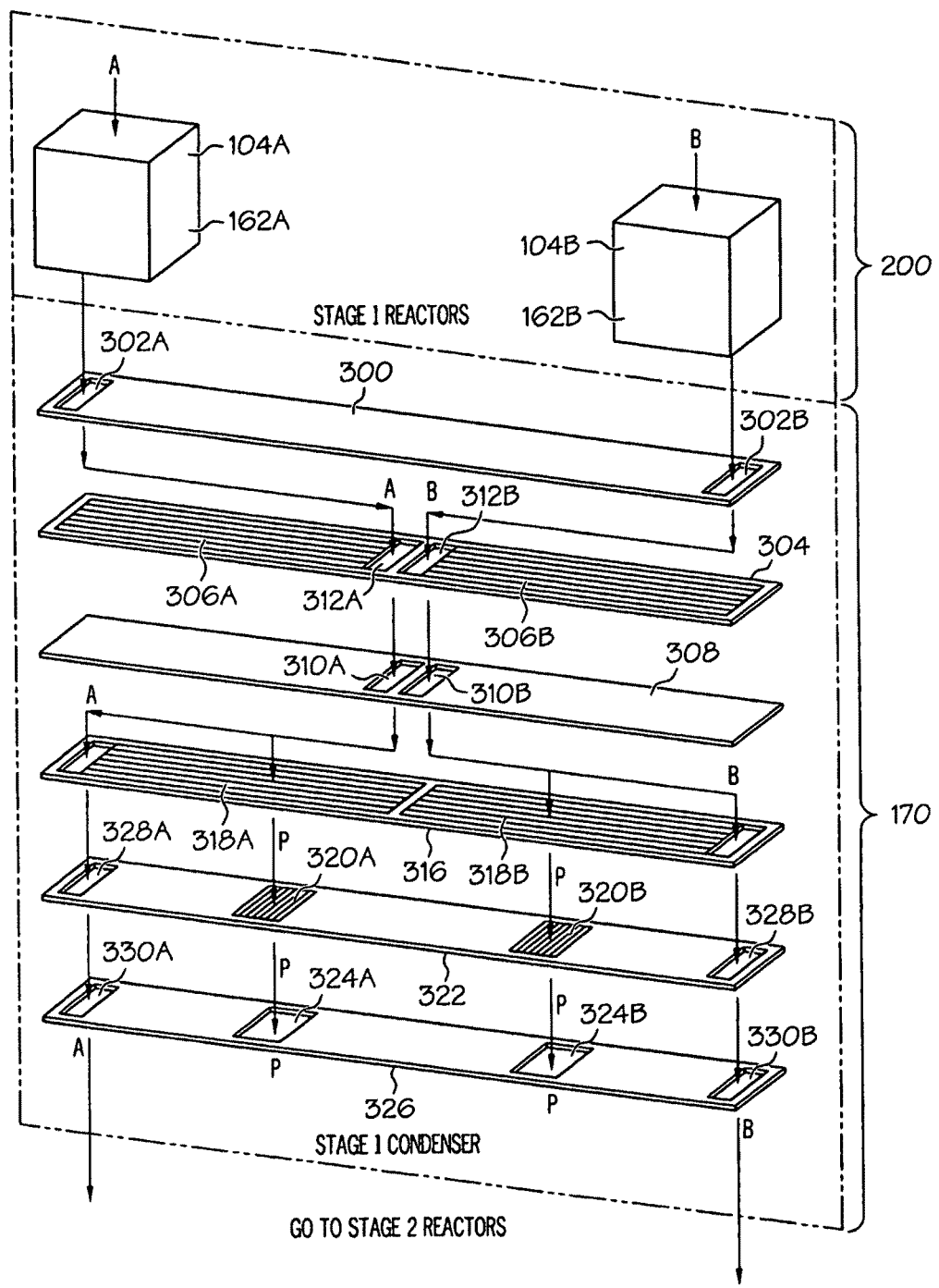
FIG. 14 is a partial exploded view of a first exemplary common condenser of an integrated microchannel unit operation in accordance with the present invention.
Figure 15:
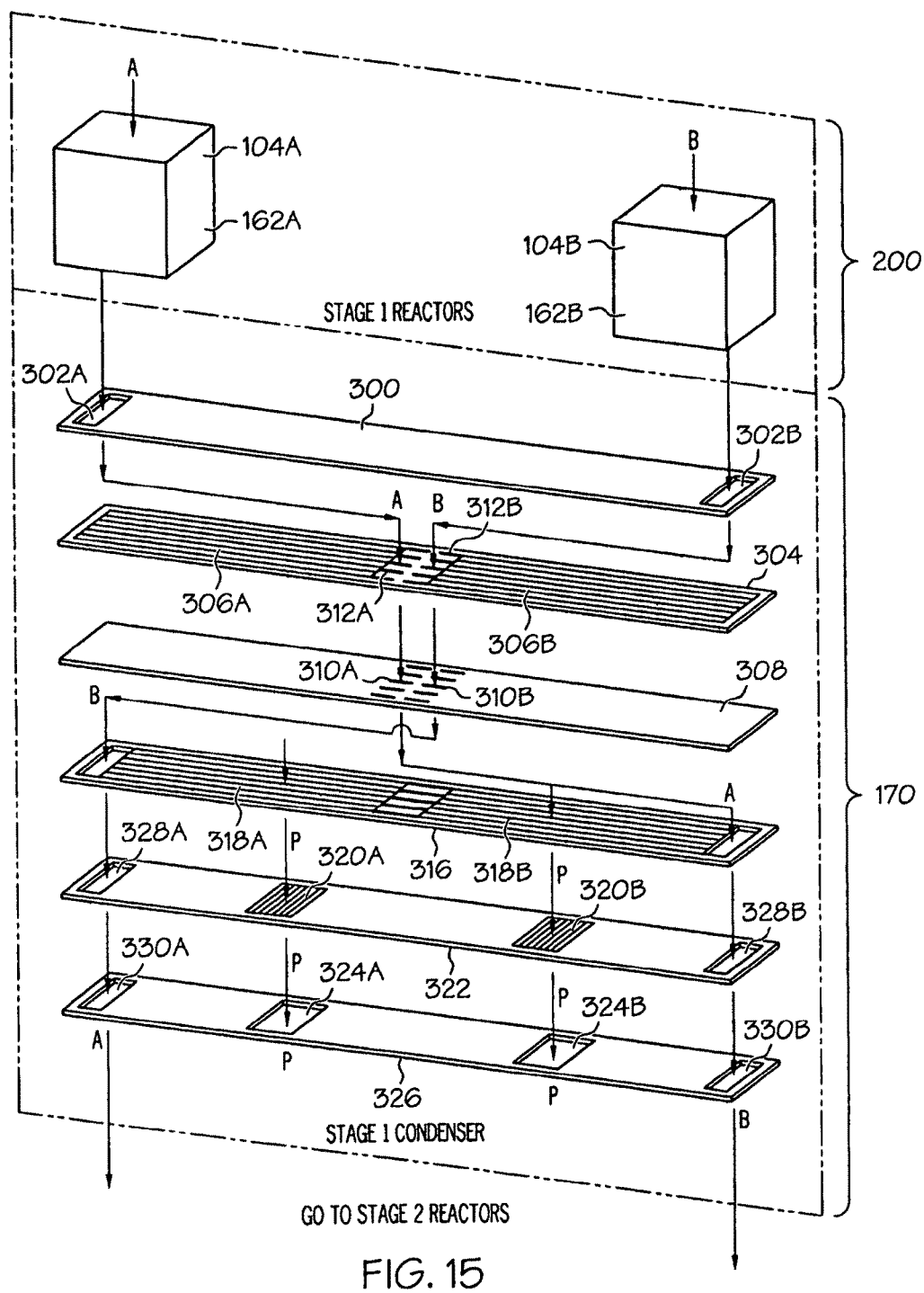
FIG. 15 is a partial exploded view of a second exemplary common condenser of an integrated microchannel unit operation in accordance with the present invention.

Referring to FIGS. 14 and 15, parallel reactors 104A, 104B may be configured to feed a vapor stream comprising methanol, unreacted syngas, and synthesis reaction by-products ("product stream") to a common microchannel heat exchanger and condenser 170. A first end plate 300 of the condenser 170 provides openings 302A, 302B therethrough for receiving the product streams from the respective first cooling stages 162A, 162B of the parallel reactors 104A, 104B. Arrow A and Arrow B represent the fluid flow of the product streams through the condenser 170. A second plate 304 adjacent to the first plate 300 includes microchannels 306A, 306B for receiving the product stream flowing through the openings 302A, 302B of the first plate at the far ends. The product stream flows along these microchannels 306A, 306B and is cooled by a cooling fluid (not shown) flowing through adjacent microchannel formed in an adjacent plate (not shown) to condense at least some of the methanol out of product stream vapor phase. A third plate 308 includes openings 310A, 310B therethrough that align with openings 312A, 312B through the second plate to deliver the two-phase product mixture to another set of microchannels 314A, 314B formed in a fourth plate 316 that includes capillary exclusion sections 318A, 318B, where the liquid phase is withdrawn through aligned microchannels 320A, 320B of a fifth plate 322. Openings 324A, 324B through a sixth plate 326 is aligned with the microchannels 320A, 320B of a fifth plate 322 and conveys the liquid products to distillation unit (not shown). The relatively dry gaseous product flowing through the microchannels 314A and 314B are recuperatively heated prior to entry of the gaseous components to the second reactor stage 202 using openings 328A, 328B, 330A, 330B. The primary difference between FIG. 14 and FIG. 15 is that the FIG. 15 shows a chiral embodiment, which is particularly advantageous when using recuperative heat exchange in the microchannel heat exchanger and condenser 170.

Figure 16:
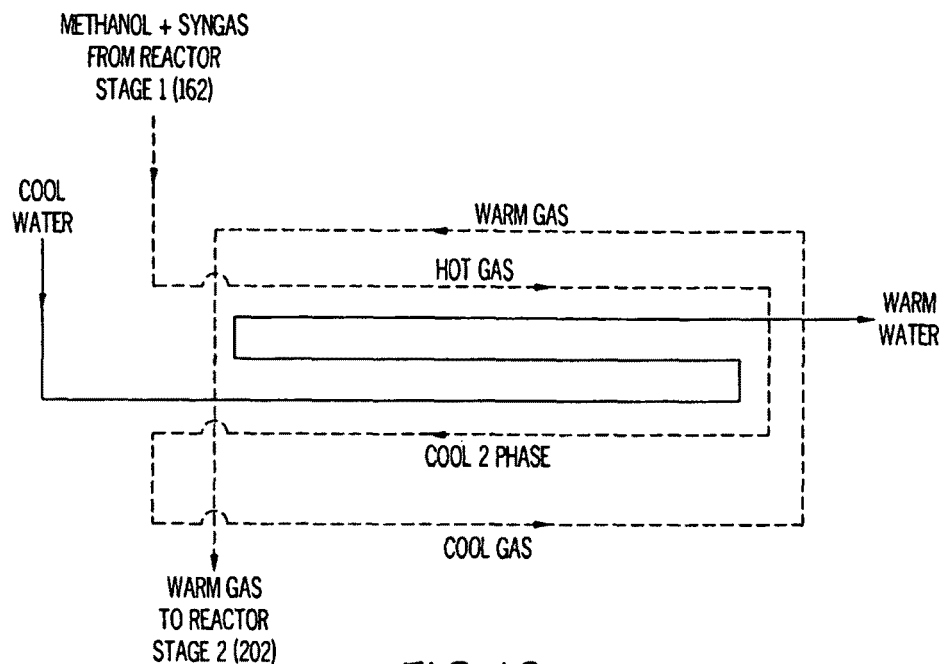
FIG. 16 is a schematic diagram representative of the flow through an exemplary condenser for use in the instant invention.

Referring to FIG. 16, an exemplary flow diagram is shown for parallel reactors 104A, 104B where recuperative heat exchange is utilized. Recuperative heat exchange involves heating the outlet gaseous stream from the microchannel heat exchanger and condenser 170 using the incoming warm stream from the first cooling stage 162. In this manner, energy from the warm stream from the first cooling stage is exchanged with the outlet gaseous stream to increase the enthalpy of this steam. This increased enthalpy is advantageous to bring about favorable reaction kinetics for increased conversion of syngas to methanol.

Referencing again FIG. 12, a second reactor stage 202 is immediately downstream from the microchannel heat exchanger and condenser 170. The microchannels of the second reactor stage 202 directly receive the gaseous reactants (syngas) from the heat exchanger and condenser 170 and introduce these reactants to a synthesis catalyst that may be packed within the microchannels, lined along the walls of the microchannels, or otherwise configured within or grown within the microchannels of the second stage 202. A grown catalyst includes one that includes a precursor in liquid solution or suspension that reacts, plates, crosslinks, or otherwise forms porous connections between the channel walls. The porosity may be macroporous, mesoporous, or microporous, or any combination of the three. As discussed previously, methanol synthesis is equilibrium dependent and withdrawal of the methanol in the condenser 170 drops the methanol concentration in the microchannels 202 that is operative to increase the frequency of reactions between the remaining syngas reactants, thereby increasing the overall conversion of syngas products to methanol on a carbon conversion basis.

A second heat exchanger and condenser 190 includes three sets of microchannels (not shown) similar to those of the first heat exchanger and condenser 170 of FIG. 13. The first set of microchannels carries a liquid water from into thermal communication with the second set of microchannels carrying the products from the second reactor stage 202. The enthalpy difference between the products and the water is such that energy is transferred from the products to the liquid water, resulting in condensation of the methanol component within the products flowing through the second set of microchannels. Condensed methanol and by-product process condensate/water from the second set of microchannels is carried away using the third set of microchannels and conveyed to the methanol distillation unit 118. The warm water produced from the heat transfer microchannels may be used to heat other process streams in the plant 100, while the remaining gaseous components of the second set of microchannels are fed to a third reactor stage 204.

A third reactor stage 204 immediately downstream from the second heat exchanger and condenser 190 includes distributed microchannels that receive the gaseous reactants (syngas) from the second heat exchanger and condenser 190 and introduce these products to a synthesis catalyst that may be packed within the microchannels, lined along the walls of the microchannels, or otherwise configured within the microchannels. As discussed previously, methanol synthesis is equilibrium dependent and withdrawal of the methanol in the condenser 190 drops the methanol concentration in the microchannels, which is operative to increase the frequency of reactions between the remaining syngas reactants, thereby increasing the overall conversion of syngas reactants to methanol on a carbon conversion basis approximating 90%. It is to be understood that this third reactor stage 204 is optional and may not necessarily be utilized in all applications.

A third heat exchanger and condenser 194 includes three sets of microchannels (not shown) similar to those of the first heat exchanger and condenser 170 of FIG. 13. The first set of microchannels carries liquid water into thermal communication with the second set of microchannels carrying the products from the third reactor stage 204. The enthalpy difference between the products and the water is such that energy is transferred from the products to the liquid water, resulting in condensation of the methanol component within the products flowing through the second set of microchannels. Condensed methanol from the second set of microchannels is carried away using the third set of microchannels and conveyed to the methanol distillation unit 118. The warm water produced in the first set of microchannels is utilized in the plant 100 as a preheating fluid or steam precursor, while the remaining gaseous components (remaining syngas reactants and byproducts) within the steam reformer 102. Using microchannel heat exchangers with embedded phase separation channels, the methanol synthesis section for a plant capacity of 1000 metric tons of methanol per day is sized to fit within one assembly 104 of roughly 1 m (wide)×1.2 m (high)×3.9 m (long). Exemplary microchannel apparatus size ranges for a methanol synthesis reactor 104 of less than 200 $m^3$ per thousand metric tons of methanol per day, or more preferably less than 80 $m^3$ per thousand metric tons of methanol per day, or even more preferably less than 10 $m^3$ per thousand metric tons of methanol per day.

Referring to FIG. 1, the methanol distillation unit 118 is operated under pressure to improve thermal integration for the overall plant 100. The range of temperatures for the 48-bar distillation unit is from 200° C. to 242° C. This compares to a distillation temperature range of 80 to 120 C at ambient pressure. The non-condensable gas stream is separated from the liquid before entering the 20-stage microchannel distillation unit 118 against a counterflow of liquid and gas. Methanol is recovered from the top sidestream of the distillation unit with a purity greater than 95%, and water is recovered from the bottom of the unit with a purity greater than 99%. The water is recycled to the coolant of the methanol synthesis reactor 104 before moving to the steam reformer 102 feed stream. The methanol distillation unit 118 uses 6 microchannel assemblies, where each assembly is 1.2 m (high) by 1 m (wide) by 3.9 m (long).

In accordance with the exemplary embodiments discussed above, ranges for methanol product purity are between 80-90%, and preferably between 95% to greater than 99%. Ranges for water purity are between 80-90%, and preferably between 95% to greater than 99%. Moreover, ranges for methanol distillation unit volume productivity are between 10 to 25 $m^3$ per thousand metric tons of methanol per day, and preferably between 25 to greater than 100 $m^3$ per thousand metric tons of methanol per day. Still further, ranges for water recycle are 25-50%, and preferably between 50% to greater than 65%.

While the exemplary distillation unit 118 has been described for distillation of methanol, other compositions could likewise be produced by the plant 100 and distilled to achieve the desired purity of products generated by other chemical reaction processes. For example, the distillation unit may be adapted to function as fractionator for separating hydrocarbons, including mixtures comprising at least one of the following types of compounds: alkanes, alkenes, alkynes, naphtalenes and other ringed compounds, aromatics, and oxygenates, including aldeydes, alcohols, ketones, carboxylic acids, and nitriles. The distillation unit may also separate mixtures comprising inorganic compounds or naturally-derived substances. The fractionator may separate close-boiling compounds, such as an ethane-ethylene fractionator or a hexane-cyclohexane separator. In exemplary form, a liquid inlet streaming containing 84% hexane and 16% cyclohexane and a vapor inlet stream comprising 9% hexane and 91% cyclohexane. The outlet liquid product stream was removed at a point slightly below the inlet vapor stream and contained 7% hexane and 93% cyclohexane. The channel generated 15 equilibrium stages in a 5-inch channel length. The temperature range over the unit varied from 69° C. to 83° C. The relative volatilities of ethane-ethylene and cyclohexane-hexane (reference ChemCAD® 5.5.0 component library) are significantly more challenging than water and methanol.

The estimation of height equivalent to a theoretical plate (HETP) as shown in Equation 2 is based on balancing the convection time and diffusion time within a microchannel. The characteristic time for convection in a single stage is defined by the stage length divided by the average fluid velocity. The characteristic time for diffusion in a single stage is defined by the square of the diffusion distance divided by the fluid diffusivity. Setting the two characteristic times equal allows solving for a simple estimate of the required HETP for phase equilibration. Similar methodologies have proven successful for diffusion to catalytic walls in chemical reactions, and by analogy were evaluated for distillation.

$$\frac{vel_{vap} \cdot t_{vap}^2}{D_{AB_{vap}}} \propto HETP_{vap} = HETP_{liq} \propto \frac{vel_{liq} \cdot t_{film}^2}{D_{AB_{liq}}} \quad (2)$$

Microchannel distillation is described in US 2006/0016216 by Tonkovich et al and is incorporated herein by reference. In microchannel distillation experiments for cyclohexane-hexane separation using the apparatus described in US 2006/0016216, a liquid film of 0.178 mm was created by flowing liquid over a woven stainless steel mesh adjacent to a 1.35 millimeter (mm) gas channel. The liquid velocity was 1 mm/second (s) and the liquid diffusivity was $5 \times 10^{-5}$ cm$^2$/s. The resulting predicted HETP for the liquid side was on the order of 0.63 cm, using Equation 2. The gas phase diffusivity was 0.0342 cm$^2$/s, the average gas velocity was 0.015 m/s, and the gaseous channel gap was 1.35 mm. The resulting predicted gas phase HETP was 0.8 cm. It was somewhat surprising that the predicted HETP in the gas phase was higher than the liquid phase, which demonstrates the importance of balancing the channel design for both fluids. Based on the change in composition, the experimental HETP was calculated at 0.83 cm. Additional experiments performed at higher velocities confirmed that the HETP was roughly inversely proportional to velocity. This is remarkable agreement for an approximate prediction of HETP and is considered a good qualitative predictor of HETP in other microchannel distillation units.

An HETP of 1 cm is utilized for the design basis of a methanol distillation unit based on the separation principles where HETP for a thin liquid film in contact with a thin gaseous film is approximated by Equation 2. However, other HETP could be utilized such as, without limitation, less than 5 cm, less than 2 cm, less than 1 cm, and less than 0.1 cm. For a film thickness of 25 microns and a velocity of 0.015 m/s, the HETP approaches 1 cm. The gaseous channel has a predicted HETP less than 0.1 cm by maintaining a gas-to-liquid channel gap ratio less than 10. By doing so, the square of the diffusion distance in the gas channel is more than offset by the three orders of magnitude reduction in the gas phase diffusivity over that in the liquid phase. HETP can be utilized to describe the efficiency of gas-liquid contacting unit operations such as distillation and absorption. Preferred ranges of HETP for this invention are less than 10 cm, or less than 5 cm, or less than 1 cm, or less than 0.5 cm.

Water co-produced with methanol inside the synthesis reactor 104 is subsequently removed from the methanol through a pressurized microchannel distillation unit 118. Methanol is purified to greater than 95% and discharged from the distillation unit 118 via a purified product conduit 198. Water from the distillation unit 118 is routed to the microchannel heat exchanger and phase separator 130.

Water is recycled within the plant 100 for the synthesis reactor 104 from three sources: from the wet syngas stream, from the methanol distillation unit 118, and optionally from the combustion exhaust stream. It is expected that the small amounts of reaction byproducts, such as alcohols, hydrocarbons, ethers, etc., in the water stream are readily reformed in the microchannel steam reformer 102 which alleviates build-up in the water recycle.

A computer simulation was utilized to scale up the plant 100 to produce 1,000 metric tons per day of methanol. For this case, each reaction section is held at the temperature and pressure condition provided in Table II. This case does not include methanol condensate removal integral with the methanol reactor unit and the corresponding temperature reduction for phase separation and recuperative heat exchange. Table I details the flow rates and heat duties of the major unit operations. For example, the total water fed to the microchannel steam reformer 102 is 39.9 metric tons/hour. Of this, only 23.3 metric tons/hour are from an independent water source because of the water capture and reuse within the system. If the water from the exhaust of the steam reformer 102 is also captured, the total amount of freshwater required would be 16.4 metric tons/hour This represents a net reduction in the total water required of 65%.

TABLE I

| Section | Unit operation | Stream | Temperature C. | Pressure (bar) | Mass flow (kg/hr) | Heat Duty (MW) |
|---|---|---|---|---|---|---|
| Reforming Section | Reformer | Air inlet | 129 | 2.1 | 161202 | |
| | | Fuel inlet | 28 | 2.1 | 15657 | |
| | | Exhaust | 250 | 1 | 176859 | |
| | | Feed (2:1 S:C) inlet | 201 | 23.5 | 119574 | |
| | | Product outlet | 300 | 21.9 | 119574 | |
| | reaction conditions | | 900 | 22 | | 113 |

TABLE I-continued

| Section | Unit operation | Stream | Temperature C. | Pressure (bar) | Mass flow (kg/hr) | Heat Duty (MW) |
|---|---|---|---|---|---|---|
| Methanol Synthesis Section | Reactor | Feed inlet | 222 | 50 | 83497 | |
| | | Product outlet | 190 | 48.8 | 83497 | |
| | | Water - section 1 | | | 114497 | 29 |
| | | Water - section 2 | | | 19216 | 5 |
| | | Water - section 3 | | | 17415 | 4 |
| Distillation Section | Distillation Unit | Subtotal water | 103 | 35 | 151127 | 38 |
| Water Capture Section | Phase Separation with HX | Feed inlet | 30 | 48.5 | 47222 | |
| | | Methanol Outlet | 200 | 48 | 43860 | |
| | | Water Outlet | 242 | 49 | 1330 | |
| | | Inlet | 30 | 48.5 | 83497 | |
| | | Gas | 30 | 48.5 | 36275 | |
| | | Liquid | 30 | 48.5 | 47222 | |
| | Product HX & Heat exchanger | Product In | 300 | 21.9 | 119573 | |
| | | Water Inlet (from distillation) | 96 | 25 | 36564 | |
| | | Water outlet (to reactor) | 188 | 24.7 | 36564 | |
| | | Product Out to compressor | 198 | 21 | 119573 | |
| Section Reforming Section | Unit operation Reformer | Air inlet | 129 | 2.1 | 161202 | |
| | | Fuel inlet | 28 | 2.1 | 15657 | |
| | | Exhaust | 250 | 1 | 176859 | |

Table II details the temperature, pressure, volume, and heat duty associated with each section of the exemplary three-section synthesis reactor 104.

TABLE II

| Zone | Temperature (C.) | Pressure (bar) | Relative Volume (%) | Heat Duty (MW) |
|---|---|---|---|---|
| 1 | 250 | 49.7 | 20 | 57 |
| 2 | 220 | 49.3 | 30 | 9.6 |
| 3 | 200 | 49.2 | 50 | 8.7 |

A second computer simulation was utilized to scale up the plant 100 to produce 1,000 metric tons per day of methanol. In this case, each of the reactor sections were maintained at a temperature of 250 C and a pressure decreasing from 50 bar at the first stage inlet to 48.8 bar at the third stage outlet. Methanol condensate removal and recuperative heat exchange was incorporated between reaction stages. Table III details the flow rates and heat duties of the major unit operations. For example, the total water fed to the microchannel steam reformer 102 is 56.6 metric tons/hour. Of this, only 33 metric tons/hour are from an independent water source because of the water capture and reuse within the system. If the water from the exhaust of the stream reformer 102 is also captured, the total amount of freshwater required would be 23.2 metric tons/hour. This represents a net reduction in the total water required of 65%.

TABLE III

| Section | Unit operation | Stream | Temperature (C.) | Pressure (bar) | Mass flow (kg/hr) | Heat Duty (MW) |
|---|---|---|---|---|---|---|
| Reforming Section | Reformer | Air inlet #230 | 129 | 2.1 | 151000 | |
| | | Fuel inlet #240 | 40 | 2.1 | 14225 | |
| | | Exhaust #252 | 252 | 1 | 165225 | |
| | | Feed (2:1 S:C) Inlet | 201 | 23.5 | 113315 | |
| | | Product outlet | 300 | 21.9 | 113315 | |
| | | At reaction Conditions | 900 | 22 | | 113 |
| Methanol Synthesis Section | Reactor | Feed inlet | 222 | 50 | 80704 | |
| | | Product Outlet | 190 | 48.8 | 80704 | |
| | | Steam Generated - Section 1 240 | 240 | 33 | 55250 | 23.5 |
| | | Steam Generated - Section 2 240 | 240 | 33 | 19800 | 7.9 |
| | | Steam Generated - Section 3 240 | 240 | 33 | 9480 | 3.8 |
| | | Subtotal - Steam Generated | | | 84550 | |
| | | Purge Gas #33 | | | 30413 | |

A third computer simulation was utilized to scale up the plant 100 to produce 1,000 metric tons per day of methanol. In this case, each of the reactor sections were maintained at a temperature of 240 C and a pressure of 33 bar. Methanol condensate removal and recuperative heat exchange was incorporated between reaction stages. Table IV details the flow rates and heat duties of the major unit operations. For example, the total water fed to the microchannel steam reformer 102 is 56.6 metric tons/hour. Of this, only 33 metric tons/hour are from an independent water source because of the water capture and reuse within the system. If the water from the exhaust of the stream reformer 102 is also captured, the total amount of freshwater required would be 23.2 metric tons/hour. This represents a net reduction in the total water required of 65%. Table V compares the results from Tables III and IV.

The overall carbon efficiency from converting a stream of natural gas to methanol is slightly more than 60% when a 3-zone isothermal methanol reactor is used with interstage product cooling and liquid recovery is included between each stage. By removing the products after each stage, the overall conversion of the 3-stage reactor can approach 90% at 250 C. This carbon efficiency is competitive with other off-shore stranded gas upgrading schemes for methanol, but lower than a conventional onshore methanol plant. The lower efficiency is a trade-off for a reduced footprint and minimized plant complexity for offshore production. Carbon efficiencies greater than 30% for a plant combining microchannel reaction and microchannel distillation units for production of methanol from natural gas certainly fall within the scope of the present invention.

with an oxygen source stream within the microchannel steam reformer 102. In an exemplary operating condition, exhaust gas from the steam reformer 102 is cooled to 30° C., where the condensed water is removed by capillary exclusion through a capillary exclusion section such as that shown in FIG. 3. For water capture from the exhaust stream, $P_1$ is roughly 103 kiloPascal (kPa). The surface tension of water is 0.0728 N/m. For example, a pore 210 radius of roughly 25 microns would allow for a differential pressure of roughly 5,000 Pa to move the liquid to a liquid collection reservoir and pumping station.

Referring to FIG. 1, another source of water that may be reclaimed comes from water that remains after steam methane reformation. Water in the wet syngas product stream is removed at pressure and sent to a collection header for the water coolant stream flowing to the methanol synthesis reactor 104. Water is also captured from the off-gas from the methanol synthesis reactor 104 by the condenser 170. Again, the separation is performed at pressure, where the condensed stream is sent to the water header for the methanol synthesis reactor 104 coolant feed, and the non-condensed stream may be sent to the microchannel distillation unit 118 as a heat source.

Figure 17:
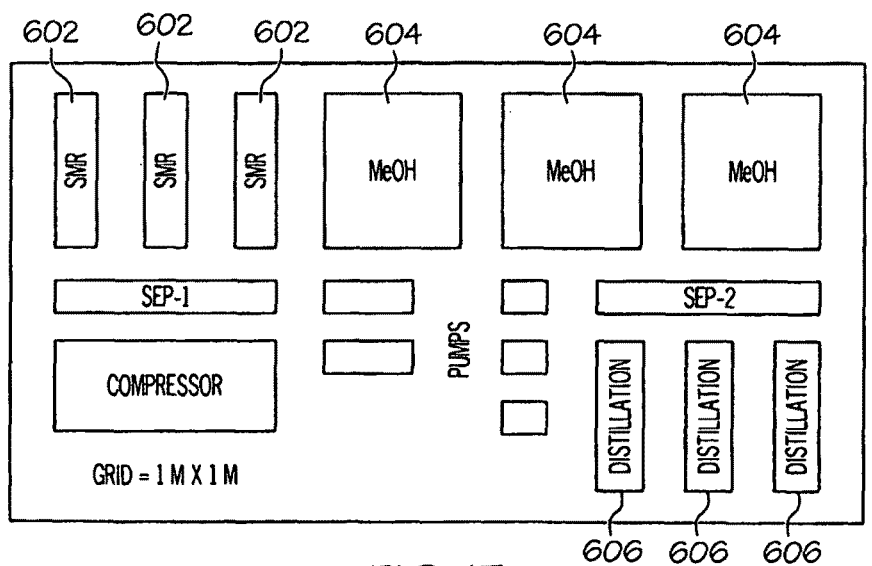
FIG. 17 is an exemplary deck layout for 1,000 metric tons per day offshore methanol synthesis plant.

Referring to FIG. 17, an exemplary application for the plant 100 of the instant invention is aboard a vessel docked to an off-shore natural gas platform. A plot plan 600 for an integrated methanol production unit of 1,000 metric tons per day has been designed to fit within an 18 m by 15 m deck. Each of the three steam methane reforming assemblies 602 includes a corresponding methanol synthesis reactor section 604. The deck size for each set of one steam methane reformers and two methanol reactor assemblies stacked on top of one

TABLE IV

| Section | Unit operation | Stream | Temperature (C.) | Pressure (bar) | Mass flow (kg/hr) | Heat Duty (MW) |
|---|---|---|---|---|---|---|
| Reforming Section | Reformer | Air inlet #230 | 129 | 2.1 | 151000 | |
| | | Fuel inlet #240 | 40 | 2.1 | 14225 | |
| | | Exhaust #252 | 252 | 1 | 165225 | |
| | | Feed (2:1 S:C) Inlet | 201 | 23.5 | 113315 | |
| | | Product outlet | 300 | 21.9 | 113315 | |
| | | At reaction Conditions | 900 | 22 | | 113 |
| Methanol Synthesis Section | Reactor | Feed inlet | 222 | 50 | 80704 | |
| | | Product Outlet | 190 | 48.8 | 80704 | |
| | | Steam Generated - Section 1 240 | 240 | 33 | 55250 | 23.5 |
| | | Steam Generated - Section 2 240 | 240 | 33 | 19800 | 7.9 |
| | | Steam Generated - Section 3 240 | 240 | 33 | 9480 | 3.8 |
| | | Subtotal - Steam Generated | | | 84550 | |
| | | Purge Gas #33 | | | 30413 | |

TABLE V

| | Isopotential Reactor Temperature, C. | Isopotential without integral HX & Sep | Isopotential with integral HX & Sep | Isothermal (250 C.) |
|---|---|---|---|---|
| Stage 1 | 250 | 71.20% | 71.20% | 71.20% |
| Stage 2 | 220 | 67.70% | 83.90% | 56.60% |
| Stage 3 | 200 | 73.00% | 81.40% | 43.80% |
| Overall | | 97% | 99% | 93% |

As discussed previously, reclamation of water produced as a byproduct of chemical reactions throughout the plant 100 may be particularly important in certain applications. One source of water comes from the combustion of natural gas another is 3.9 m×1 m by 6.3 m high. The nine assembly stacks fit across 18 m of vessel deck space, where roughly 1 m is allowed between assembly stacks for maintenance access. A set of distillation assemblies 606 requires an approximately 3.9-m by 12-m footprint and is roughly 1 m high. Again, 1 m of deck space is allowed between distillation assemblies for maintenance access. The resulting combination of microchannel units and conventional equipment easily fits within an 18-m by 15-m deck footprint. The plant plot plan also includes a compressor, pumps, control system, additional heat exchangers This is in stark contrast to the deck space that would otherwise be required for non-microchannel technology.

The size of a 1,000 metric tons per day methanol plant with 30 full-scale reactor blocks housed within six assemblies would be 3.9 meters (m)×5.8 m x 3.9 m. The complete system for this plant, at the performance values of 18 Watts (W)/square centimeter ($cm^2$) heat flux in the reforming reaction section and roughly 14 $m^2$ of area for reaction heat transfer per reactor, would require nine SMR assemblies of five reactors per assembly. Each assembly as integrated for an offshore methanol synthesis reaction system would be roughly 3.9 m (long) by 3.9 m (high) by 1 m (wide).

Figure 18:
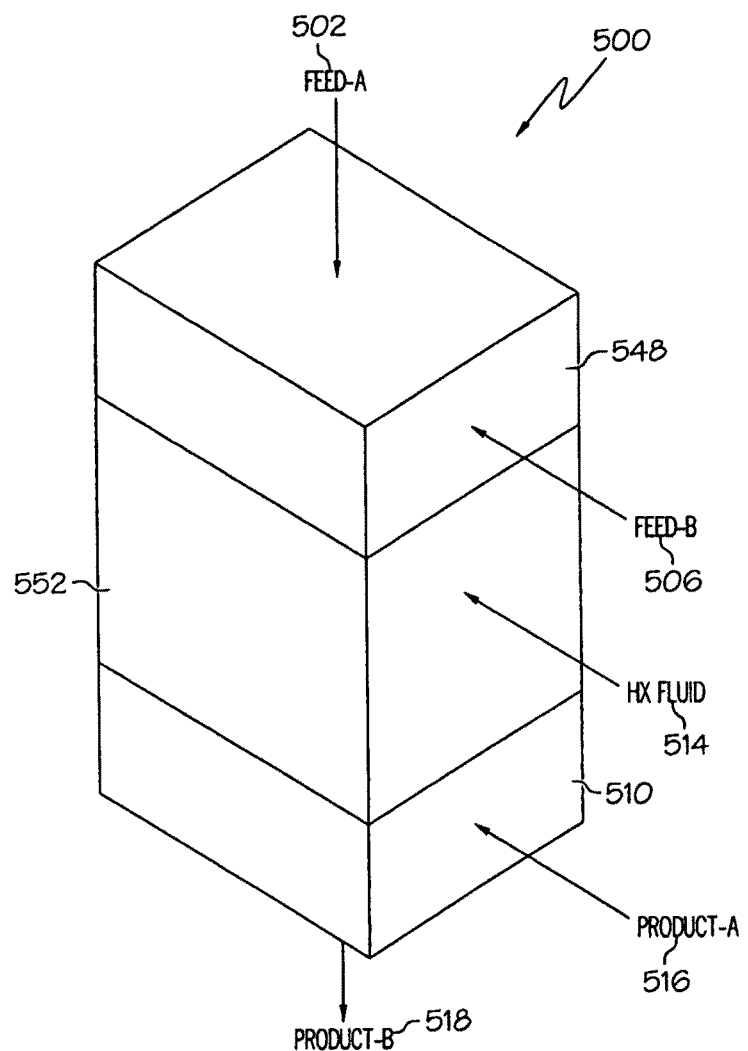
FIG. 18 is an elevated perspective view of an integrated microchannel unit housing multiple unit operations.

Referring to FIG. 18, while the primary example discussed above has been for methanol synthesis, the present invention is equally useful for combining multiple unit operations into a single block 500 or multiple subassemblies into an integrated reactor block 500. It may be preferable to assemble an integrated reaction or separation system with multiple unit operations that may use two ore more unique boxes that are stacked and assembled to form a single component after assembly.

In this example, a single feed stream 582 enters the top of the distribution and mixing section 548, while a second feed stream 506 enters from the side and is mixed with sufficient uniformity into the first feed stream 582 prior to entering a reactor section 552. A heat exchange fluid stream 514 enters the reactor section 552 and is in thermal communication with the microchannels of the reaction section 552 in which the chemical reactions are carried out. The resulting product from the reaction section 552 is fed to a separation and heat exchange section 510 that is mated to the end of the reactor section 552, where the heat exchange section 510 includes two product streams 516, 518 exiting therefrom.

Referencing FIGS. 5, the sections 548, 552, 510 are fabricated from shim or laminates and are preferentially partially etched to allow the channel flow path to extend all the way to the end of the subassembly in a manner similar to the synthesis reactor 104. The features and thus flow passageways have at least one dimension that is in the microchannel dimension. The outlet of at least one of the fluids extends to the end of the device (as shown in the first and fourth laminates from left to right in the above figure). By extending to the end of the device the flow passageways may be aligned with the flow passageway in the second type of subassembly such that a fluid may travel without substantial flow collection and redistribution. By substantial flow collection and redistribution it is possible that up to 20% of the flow in any one channel, and less than 10% more preferred, and less than 2% still more preferred of the fluid in any one channel would move to a passage way other than the corresponding flow channel in the second assembly. In one embodiment, channels may mostly map one to one from the first and second assemblies, where the fluid exiting each channel in the first subassembly maps to one channel in the second subassembly. In alternate embodiments, the fluid from two or more channels in the first subassembly maps to one channel in the second subassembly. In an alternate embodiment, the fluid from one channel in the first assembly may map to two or more channels in the second subassembly. Fluid does not substantially leak or travel orthogonally in the plenum separating the first and second subassembly to other channels. The fluid does not substantially collect from a multitude of small channels into one large channel that then changes flow direction to redistribute to a second array of channels in the second sub assembly. The first and third sections 548, 510 mate with the second section 552 so that the flow path through all three sections 548, 552, 510 extends throughout without substantial flow consolidation.

There are multiple methods of mating or joining the two assemblies (548 to 552 or 552 to 510) as shown in FIGS. 8-11. In a first embodiment 600 shown in FIG. 8, the channels in the first section 548 or 552 (represented in FIG. 8 as 502) undergo a reduction in channel cross section near the outlet of the channel in the first section 548 or 552 and abuts the inlet to the second section 552 or 510 (represented in FIG. 8 as 504). By this method, the tolerancing of the two channels is eased such that the precise placement of the first channel next to the second channel in the first and second sections respectively may have a larger degree of error and still create an unobstructed connection between fluid channels in the first and second sections.

Figure 9A:
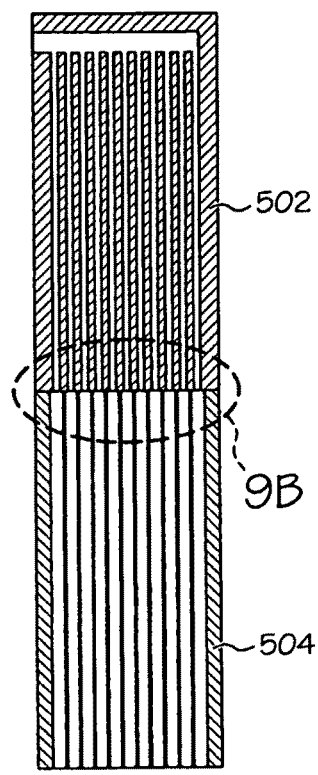
FIG. 9 is a cross-sectional view of a second exemplary interface between microchannel unit operations or sections of a microchannel unit operation.
Figure 9B:
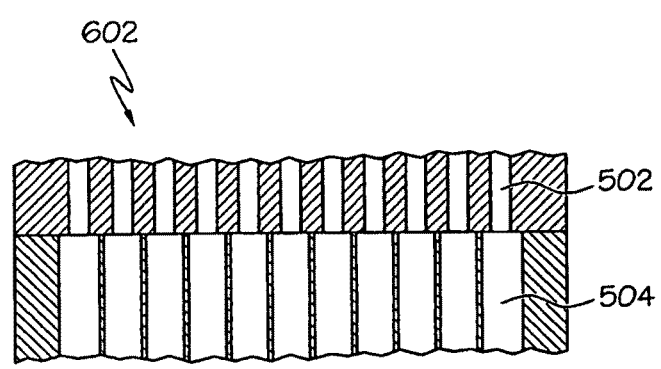

Referring to FIG. 9, in a second exemplary embodiment 602, the flow channels on the first section do not have a reduction in cross section at a local point, but rather have a smaller cross section all through the flow length in the first assembly such that at the connection point the channel dimension of one of the channels in the first and second subassembly are smaller than the other to ease the challenge of alignment.

Figure 10A:
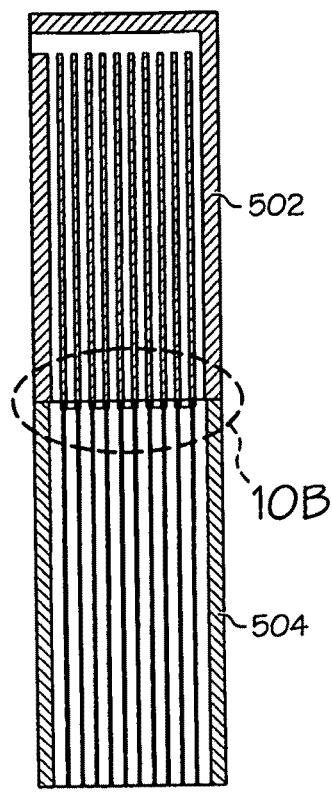
FIG. 10 is a cross-sectional view of a third exemplary interface between microchannel unit operations or sections of a microchannel unit operation.
Figure 10B:
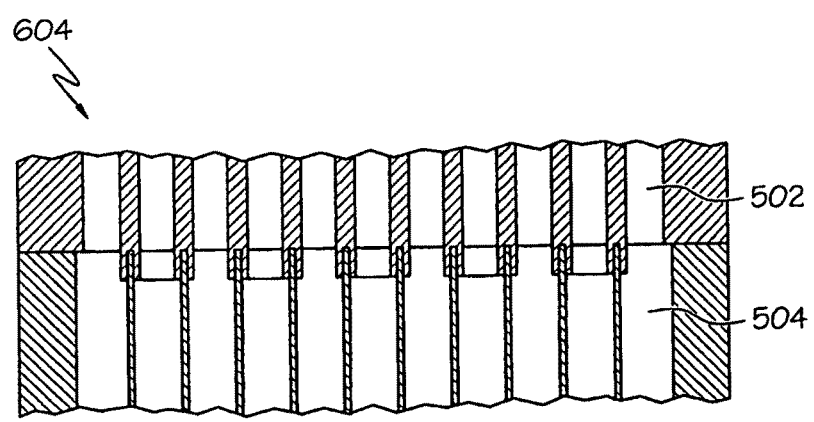

Referring to FIG. 10, in a third exemplary embodiment 604, the fluid channels for the first section are designed to create a groove that extends in the metal between the channels such that the groove fits over the waveform for positive alignment. The groove would be oversized from the tongue such that alignment would be straightforward.

Figure 11A:
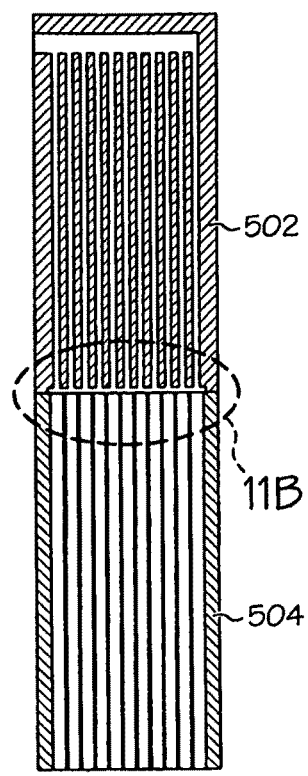
FIG. 11 is a cross-sectional view of a fourth exemplary interface between microchannel unit operations or sections of a microchannel unit operation.
Figure 11B:
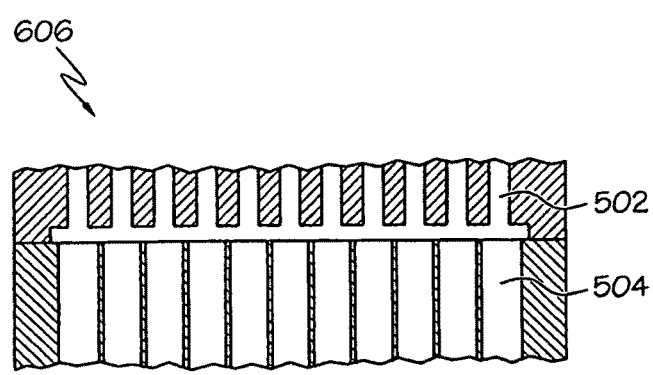

Referring to FIG. 11, in a fourth exemplary embodiment 606, an open plenum separates the fluid channels between the first and second sections. For this example, the fluid travels substantially straight from the first to the second sections. The fluid does not substantially redistribute within plenum that separates the first and second subassembly. The fluid maps in a regular manner from channel to channel between subassemblies or from one channel to two or more or from two or more channels to one respectively between the first and second sections.

An additional advantage for the joining of two sections, even two sections made in the same style but joined after each individual section is joined may rise from the ease of catalyst or sorbent integration. The ability to break a device at a point other than an end may enable the use of adding or removing and reloading a catalyst or sorbent. This approach may also make possible the use of replacing a core of a reactor or sorbent without losing parts of the section. If the catalyst in the second section were to become fused and unable to be removed from the second section, then a new section or second section could be added or integrated with the old first section to put the device back into service. This approach may also be useful for single phase or multiphase applications. Unit operations that may be advantaged by this approach include chemical reactions, heat exchange, mixing, fluid distribution, separations, distillation, absorption, adsorption, classification, and others.

It is also within the scope of the invention for one or more integrated microchannel unit operation blocks to be housed within a pressurized containment vessel. Exemplary vessels include those disclosed in U.S. patent application Ser. No. 10/774298 (U.S. 2005/0175519 published on Aug. 11, 2005), the disclosure of which is hereby incorporated by reference.

Referring back to FIGS. 4-6, an alternate exemplary reaction, commonly referred to as a Fischer-Tropsch (FT) reaction, may be carried out high aspect ratio microchannels using the structures shown. For purposes of the instant disclosure, high aspect ratio comprises a height to width ratio greater than about 2. In this exemplary reaction, the first reactor stage 152 carries out a chemical reaction in which carbon monoxide and hydrogen are converted into liquid hydrocarbons of various forms. This FT reactor 148 incorporates a corrugated insert 700 fabricated from a high thermal conductivity material (i.e, a material having a thermal conductivity greater than 20

W/m-K). The first set of microchannels 154 are formed cooperatively using the right angle corrugated insert 700 sandwiched between opposing planar sheets 702 to have a longitudinal channel length of approximately one to sixty inches. However, it is also within the scope of the invention to utilize microchannel lengths greater than sixty inches. In this manner, each microchannel is defined on three sides by the corrugated insert and on the fourth side by one of the planar sheets. Thus, heat produced within the microchannels 154 during the FT reaction may also flow through the corrugated insert 700 longitudinally in the direction of fluid flow to further suppress hot spots and reduce the likelihood of dry out on the coolant channels 158. In exemplary form, the coolant microchannels 158 house water that is partially boiled to remove the heat of the FT reaction.

As will be apparent to those skilled in the art, the sizing of cooling channels 158 may depend on the required overall heat transfer duty as well as the required heat flux of the insert 700 and sheets 702. Moreover, the entire reactor 148 may be fabricated from a high thermal conductivity material such as copper. Exemplary dimensions for the instant reactor 148 include reaction microchannel heights of approximately 0.125 inches, widths of approximately 0.04 inches, and lengths of approximately 1 to 60 inches. Moreover, exemplary sheet 702 thickness are approximately 0.02 inches, while exemplary corrugated insert thicknesses (of the sheet itself) are approximately 0.006 inches.

Figure 19:
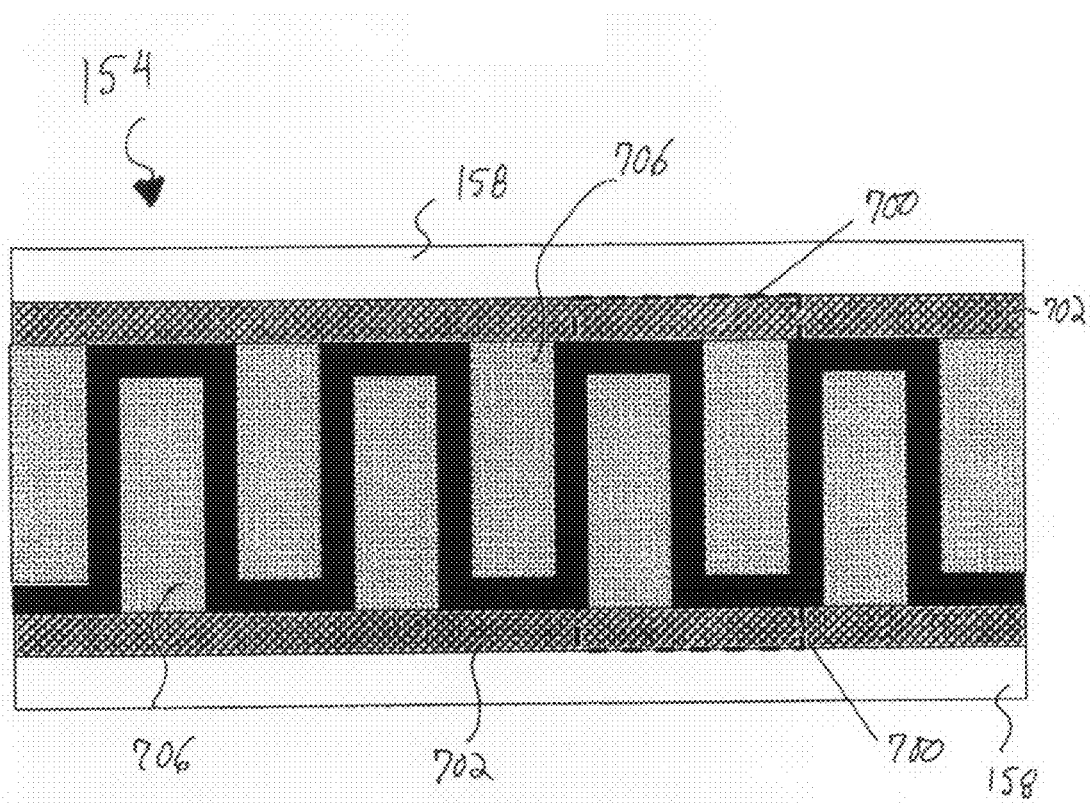
FIG. 19 is an exemplary partial cross-section of the reactor of FIGS. 4-6.

Referring to FIG. 19, an exemplary partial cross-section of the reactor of FIGS. 4-6 includes an FT catalyst 706, in a particulate form, packed within the microchannels 154 to substantially span the gap between opposing heat transfer walls. As discussed previously, the lateral sides of each microchannel 154 comprise the corrugated insert 700, while the top and bottom of each microchannel comprise the insert and the planar sheet 702. The repeating unit of this microchannel reactor 154 is denoted by the dotted line. In alternate exemplary embodiments, the corrugated insert 700 may be used in conjunction with a single planar sheet 702 and corresponding microchannels 158, so that a majority of heat from the FT reaction flows toward the heat transfer microchannels 158. The FT catalyst particles 706 are preferably maintained at a size so that a minimum of two average catalyst particle diameters may span between opposed sidewalls of the insert 700. For example, a primary dimension (i.e., average diameter) of the catalyst particle 706 may be at least three times smaller than the distance between opposing sidewalls of the insert 700. However, smaller catalyst particles 706 may be utilized to provide a ratio less than 1:1 of opposing wall width of the insert 700 to particle diameter. In other words, for opposing wall distance of roughly 1 mm, a particle diameter of 500 microns or less would be in order, such as 300 microns and smaller (including 100 microns or smaller). In this manner, the exemplary reactor 148 allows a higher mass of catalyst to be added to a fixed reactor volume, thereby enabling a higher volumetric production rate from the reactor having a non-Taylor flow pattern.

In a further alternate embodiment, the FT reactor 148 may be partially packed with both a catalyst 706 and an inert material (not shown) within the microchannels 154. The inert material may be packed at either the top, bottom or both of the reaction channel in a region that is not directly adjacent to cooling microchannels 158. In some exemplary embodiments, the inert is removed and replaced with catalyst because the reaction heat generated in these zones that are not intimately adjacent (in the same axial plane) with the cooling microchannels 158 may travel longitudinally (or axially) down the high thermal conductivity insert 700 to the available cooling microchannels 158 either downstream (for the case of the catalyst packed at the leading edge of the reactor) or upstream (for the case of the catalyst packed at the outlet face of the reactor). The packed catalyst may be retained by the use of a foam or screen material that abuts the top and or bottom of the reactor face that opens to the insert 700. The abutting material has mean openings that are smaller than the average particle size of the particulate catalyst 706.

Figure 20:
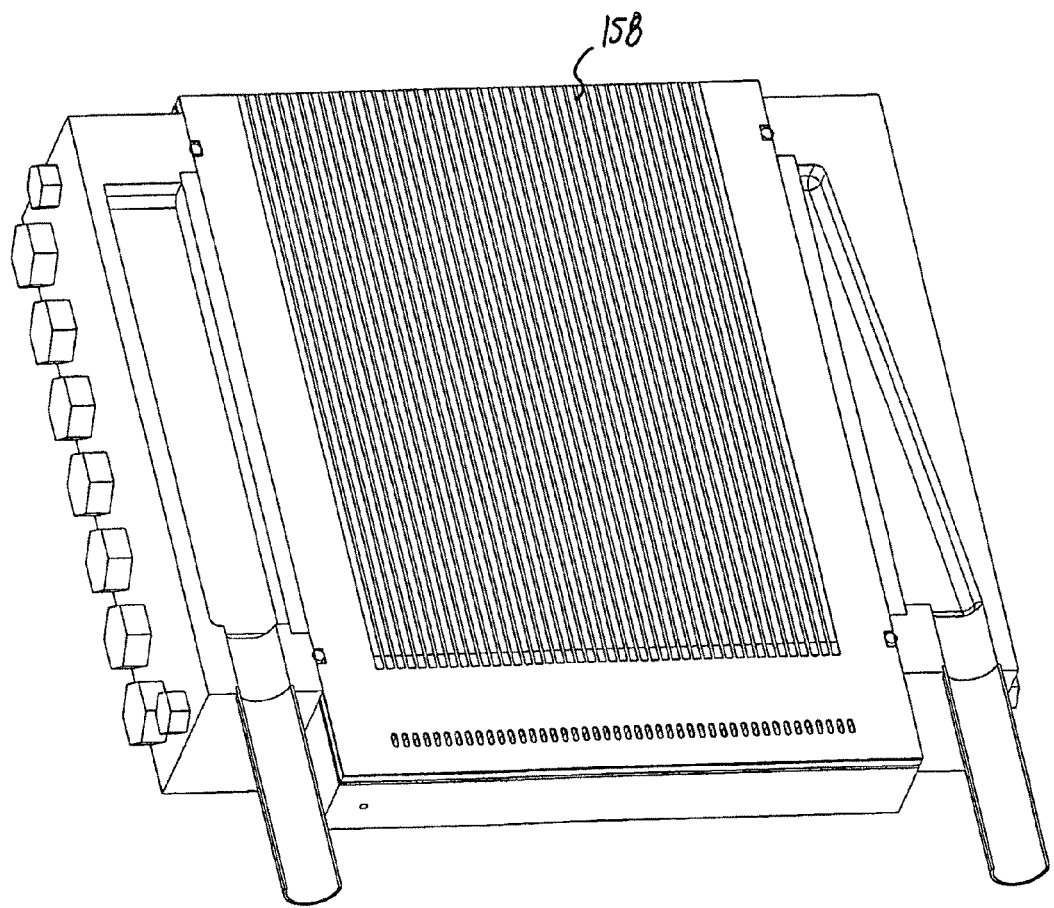
FIG. 20 is an exemplary a footer or manifold for use with the instant invention that gathers the flow from more than one parallel microchannels.

Referencing FIG. 20, the outlet face of the FT reactor 148 is joined to a footer that gathers the flow from more than one parallel microchannels and permits transference to a collection pipe. The product footer is preferably designed with an angle or taper to ease the free flow of liquids and waxes that are co-produced in the reaction. The angle of inclination as measured from a parallel plane to the outlet face of the reactor is preferably greater than 1 degree, more preferably greater than 5 degrees, and more preferably still greater than 10 degrees. In some preferred embodiments, a footer may have more than one angle of inclination and may drain to a center, side, or other port that connects to the outlet face of the FT reactor 148.

Figure 21:
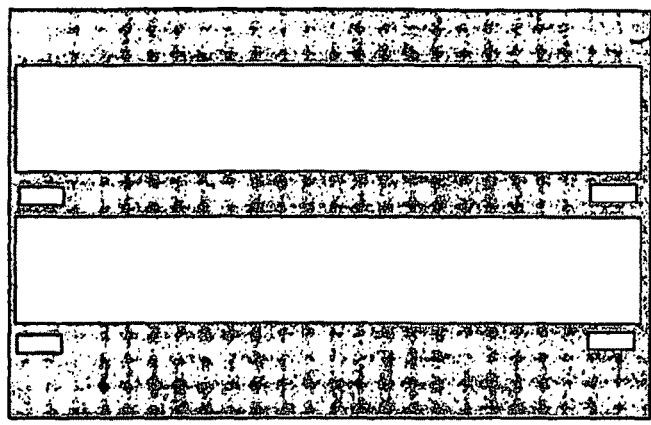
FIG. 21 is an exemplary shim or sheet for fabricating a microchannel reactor in accordance with an exemplary embodiment of the instant invention.
Figure 22:
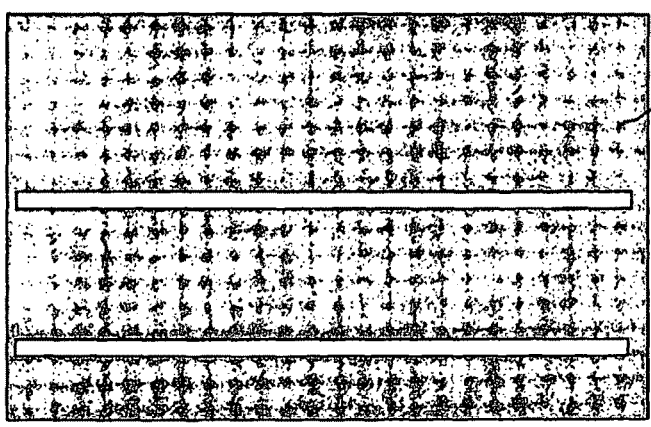
FIG. 22 is an exemplary shim or sheet for fabricating a microchannel reactor in accordance with an exemplary embodiment of the instant invention.

Referring to FIGS. 21 and 22, an alternate FT reactor 800 may be fabricated using a plurality of laminates 802, 804. Each figure shows a separate shim pattern fabricated from copper shims that, when stacked in an A,B,A,B,A,B pattern, create a reactor 800 that would be sized to have 1 mm wide FT reaction microchannels (similar to those shown in FIG. 19) and 0.5 mm wide cooling microchannels (similar to those shown in FIG. 19). The height of the microchannels in the upper shim (FIG. 21) may range from 1 to 20 mm. The height of the cooling microchannels in the lower shim (FIG. 22) may range from 0.05 mm to 5 mm. After bonded, brazed, or otherwise joined in an intimate fashion, the reactor 800 would preferably have the left and right sides cut off to open the tall channels to receive the FT catalyst. Two endplates (not shown) are added to either side of the reactor 800. Each endplate includes inlet and outlet connections to manifold in water or another cooling medium. The cooling mechanism may utilize boiling or convective heat transfer. This reactor 800 accommodates the co-flow of coolant (or counterflow) to match the highest rate of heat removal with the highest generation point of heat removal at the top of the reactor bed.

Figure 23:
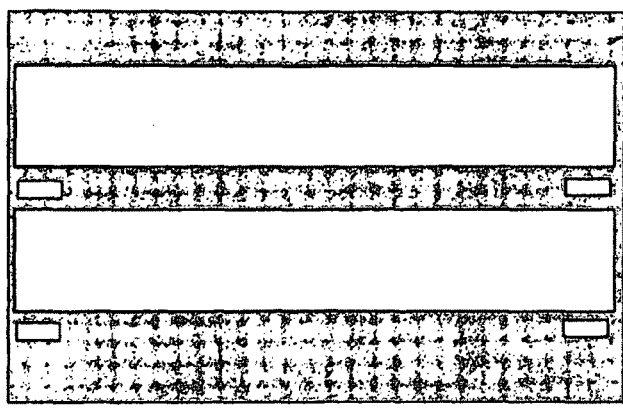
FIG. 23 is an exemplary shim or sheet for fabricating a microchannel reactor in accordance with an alternate exemplary embodiment of the instant invention.
Figure 24:
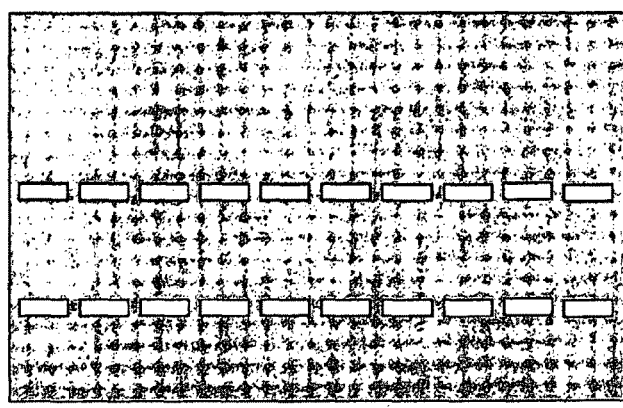
FIG. 24 is an exemplary shim or sheet for fabricating a microchannel reactor in accordance with an alternate exemplary embodiment of the instant invention.

Referring to FIGS. 23 and 24, an alternate FT reactor 820 may be fabricated from shims 822, 824 to make an integral FT reactor in an semi-ortho pattern, where the flow of the heat transfer fluid traverses orthogonal to the shim thickness direction.

Referencing FIGS. 25-30, model calculations were performed on the exemplary repeating units (shown in exemplary form in FIG. 19 using a dotted outline). The boundaries of this repeating unit are cut through the middle of the copper ribs. The model domain extends to the full length of the process channels. Several boundary conditions are presumed for purposes of the calculations, such as, without limitation, periodic wall boundary on two sides, constant temperature on walls facing the cooling channels (which is set at 220 C), a mass flux is specified to give 300 microseconds contact time, the $H_2$ to CO ratio in the feed is 2 and 10% $N_2$ as balance, the feed temperature is set to the same value as wall temperature, and finally, the pressure at the exit of the reactor is set to 350 psi. In addition, the catalyst bed characteristics are presumed to exhibit a void fraction of approximately 0.35, and have an effective thermal conductivity of approximately 0.3 W/m-K.

The complex FT reaction system is modeled using six reactions which are shown in FIG. 25. The reactions producing $C_1$ to $C_4$ are modeled separately to account for the fact that the ideal ASF product distribution is not applicable below $C_4$.

The FT product is modeled as $C_{14}$. The carbon number of 14 is the result of averaging all products $C_5$+assuming ASF product distribution with chain growth probability as 0.9.

This set of kinetics gave reasonable agreement with the test data. The rates are based on unit catalyst mass. The reactions on the porous media are modeled as volumetric reactions. In order to convert the rates to unit volume based rates, the catalyst loading value in the unit of kg-cat/m3 is multiplied to the pre-exponential factors. The catalyst loading level is chosen to target 70% CO conversion. The value is 1980 Kg-cat/m3. The intent of varying the catalyst loading level is a surrogate for evaluating the impact of intrinsically more active catalysts and the ability for the reactor design to manage the heat.

The overall reactor performance for a six inch long reaction microchannel is as follows:
  CO conversion: 69.2%
  CH4 selectivity: 15.6%
  Maximum temperature rise in the catalyst bed: 4.3 C
  Location of maximum temperature: in the catalyst bed 0.3" from the beginning of the catalyst bed
  Maximum heat flux on the heat transfer wall: 1.32 W/cm2
  Location of maximum heat flux: 0.3" from the beginning of the catalyst bed.

Figure 26:
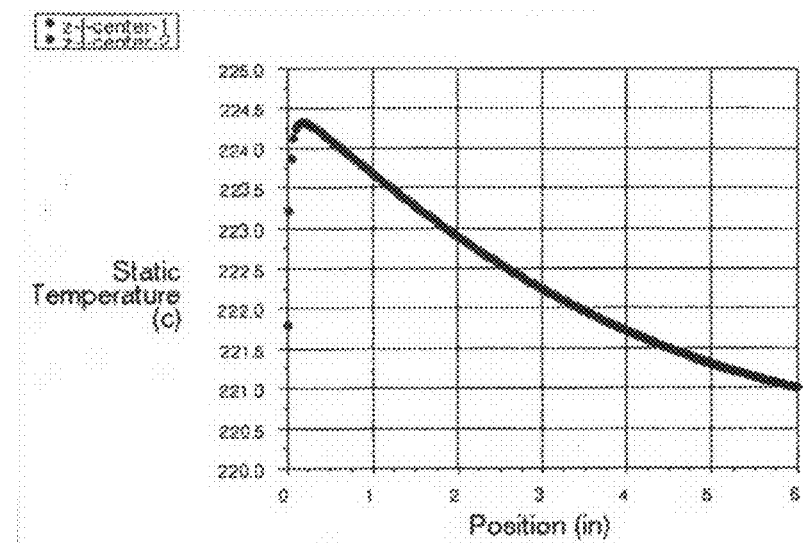
FIG. 26 is an exemplary plot showing temperature profile in a catalyst bed.

Referring to FIG. 26, a calculated temperature profile in the catalyst bed is shown by plotting the temperature in the bed as a function of reactor length along the center of the bed. From this plot, the maximum temperature and its location can bed easily determined.

Figure 27:
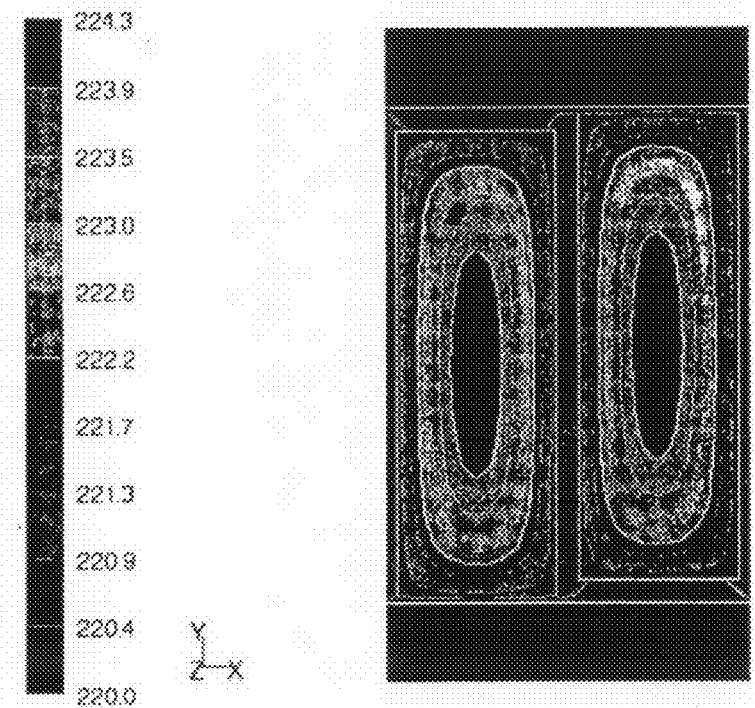
FIG. 27 is an exemplary graph showing temperature distribution at a cross section located 0.3 inches from the beginning of the catalyst bed.

Referencing FIG. 27, a calculated temperature distribution at a cross-section of the reaction microchannels is shown by plotting the temperature in the bed as a function of position. From this plot, it is revealed that the dominant heat transfer distance in this reactor is half of the spacing between the copper ribs. The ribs act as a heat transfer super-highway to quickly remove the heat out of the reaction zone.

Figure 28:
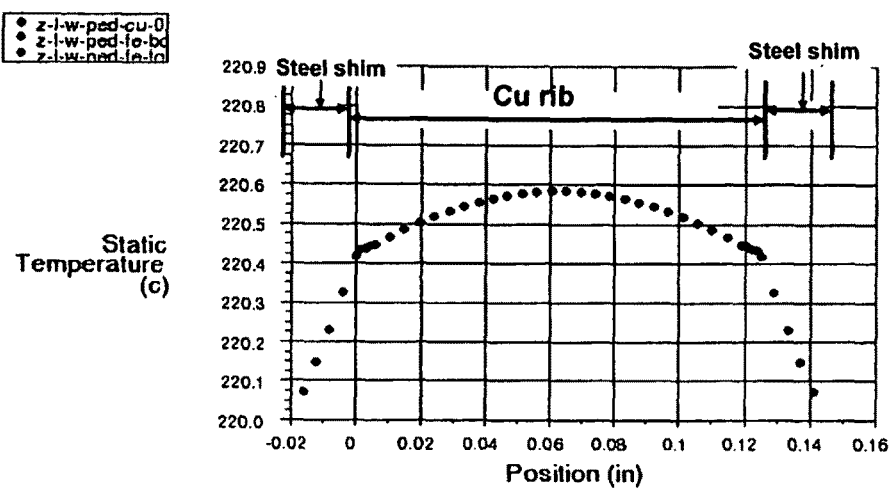
FIG. 28 is an exemplary plot showing temperature profile along the corrugated insert three 0.3 inches from the beginning of the catalyst bed.

Referring to FIG. 28, a calculated temperature distribution profile within the reactor is shown by plotting temperature as a function of position of the components within the reactor. Although the reaction heat is transferred out of the reaction zone dominantly by the copper corrugated insert, the temperature variation along the lateral walls of the insert is small due to the high thermal conductivity of copper. Temperature distribution along the copper in the channel height direction shows small temperature variation less than 0.2 C from the center (largest T) to the edge (smallest T) of the wall. In comparison, the T difference along the center of the catalyst bed is ~4 C.

Heat flux distribution was also calculated for the exemplary reactor structure shown in FIG. 19. Results from the periodic solution created by a corrugated insert for the catalyst under the described operating conditions are as follows:
  On the top sheet adjacent to the corrugated insert:
  Total heat removed: 2.23 W
  Average heat flux: 0.57 W/cm2
  On the corrugated insert walls facing the sheet:
  Total heat removed: 1.33 W
  Average heat flux: 0.68 W/cm2
  On the top sheet adjacent to the catalyst:
  Total heat removed: 0.9 W
  Average heat flux: 0.46 W/cm2

From these results it can be shown that: (1) the total heat flow through the sheet layer is uneven; and (2) a higher heat flux through the sheet adjacent to the corrugated insert than through the sheet adjacent to the catalyst.

Figure 29:
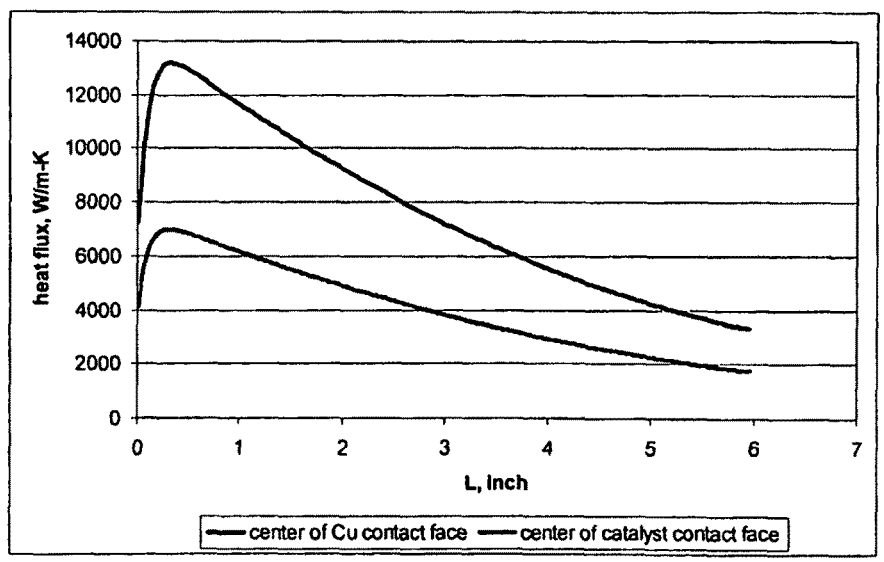
FIG. 29 is an exemplary plot showing heat flux profiles along the reactor length, with the top curve corresponding to the center of the corrugated insert facing section, while the lower curve corresponds to the center of the catalyst facing section.

Referring to FIG. 29, the heat flux profiles along the reactor length are plotted for two locations. The blue curve is at the center of copper rib facing section and the green curve is at center of catalyst facing section. At any reactor length, the former location gives the maximum heat flux and the latter location gives minimum heat flux value. From these curves the maximum heat flux value on the top wall and its locations can be read.

Figure 30:
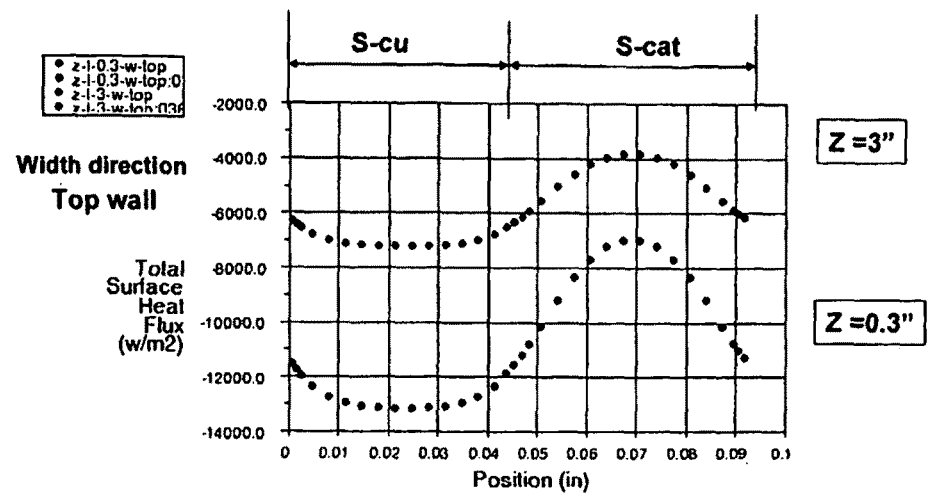
FIG. 30 is an exemplary plot showing heat flux profiles on top wall of the reactor in lateral direction, where the top curve corresponds to 0.3 inches from the beginning of the catalyst bed, while the lower curve corresponds to 3 inches from the beginning of the catalyst bed.

Referencing FIG. 30, a plot shows the heat flux distribution along the lateral direction on the top wall. Heat flux is plotted at two locations. Black curve—0.3" from the beginning of the catalyst bed, red curve—3" from the beginning of the catalyst bed. At the rib facing section, the profile is more flat.

The overall reactor performance for a twenty-two inch long reaction microchannel is as follows:
  CO conversion: 70.0%
  CH4 selectivity: 15.5%
  Maximum temperature rise: 4.7 C
  Location of maximum temperature: in the catalyst bed 0.5" from the beginning of the catalyst bed
  Maximum heat flux on the heat transfer wall: 1.5 W/cm2
  Location of maximum heat flux: 0.5" from the beginning of the catalyst bed.

Figure 31:
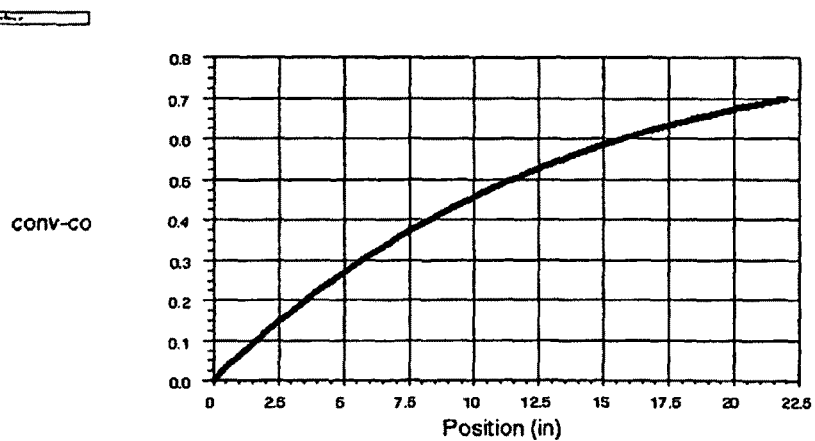
FIG. 31 is an exemplary plot showing carbon dioxide conversion along the reactor length.
Figure 32:
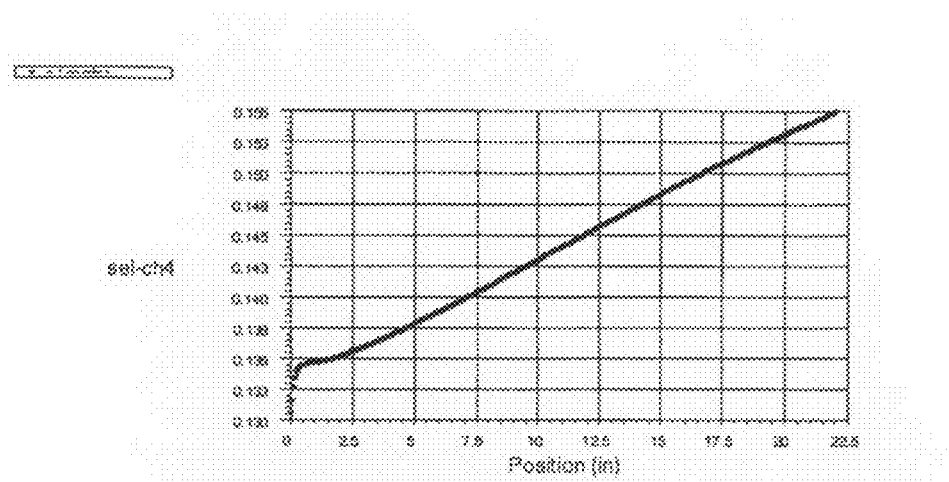
FIG. 32 is an exemplary plot showing methane selectivity along the reactor length.

The temperature and heat flux distributions are similar to the exemplary six inch reactor. Likewise, the conclusions drawn for six inch reactor are also applied to the twenty-two inch reactor. In this regard, FIG. 31 shows the CO conversion along the reactor length. The curve is flat toward the end of the reactor. FIG. 32 shows the $CH_4$ selectivity along the reactor length. It increases from 13.3% at the beginning to 15.5% to the end.

In the above exemplary embodiments, as discussed with respect to FIGS. 19-32, it was presumed that the interface between the corrugated insert 700 and the opposing planar sheets 702 was resistance free, as well as between the corrugated insert 700 and the catalyst 706. In other words, it was presumed that no gap existed between the corrugated insert 700 and the planar sheets 702 so that conductive heat transfer was the sole means of thermal transfer. Nevertheless, it has been found that: (1) if there is decreased physical contact between the corrugated insert and the adjacent sheets at the same axial location for more than half an inch, the impact is insignificant on the overall FT predicted performance; (2) if the decreased physical contact occurs only on one full side of the corrugated insert and its adjacent sheet, the impact is insignificant on the overall FT predicted performance; (3) if the decreased physical contact between the catalyst and corrugated insert occurs only on one side of the microchannel, the extent of it, either over the whole length of the reactor or over a small length of the reactor, the impact is insignificant on the overall FT predicted performance; and (4) if the decreased physical contact between adjacent structures occurs at locations far away from the potential high temperature region, near the inlet of the reactor for this reaction system, the impact is insignificant on the overall FT predicted performance.

Figure 33:
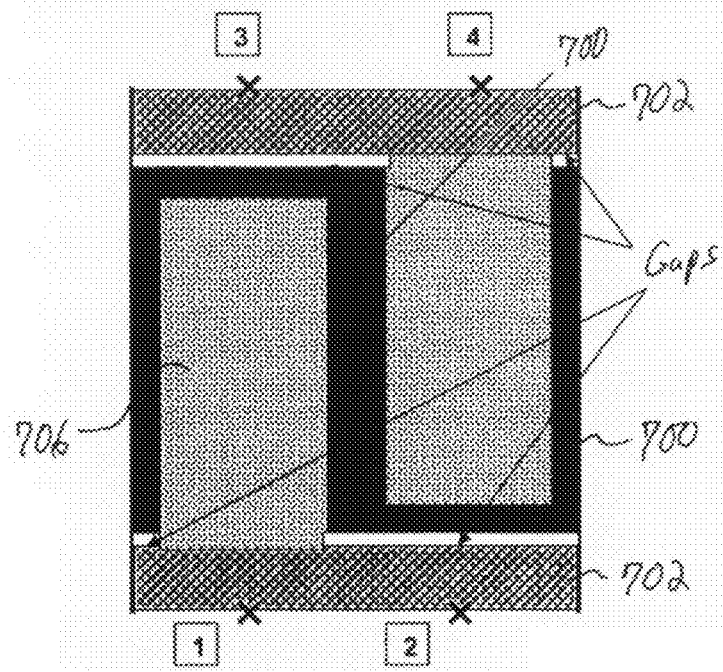
FIG. 33 is an exemplary plot showing the thermal resistance layers between copper corrugated insert and sheet walls. Four locations on the sheet walls are marked for temperature and heat flux plotting, with area #1 corresponding to the middle of corrugated insert facing section on the top wall, while area #2 corresponds to the middle of catalyst facing section on the top wall, while area #3 corresponds to the middle of catalyst facing section on the bottom wall, and finally, area #4 corresponds to the middle of corrugated insert facing the bottom wall.
Figure 34:
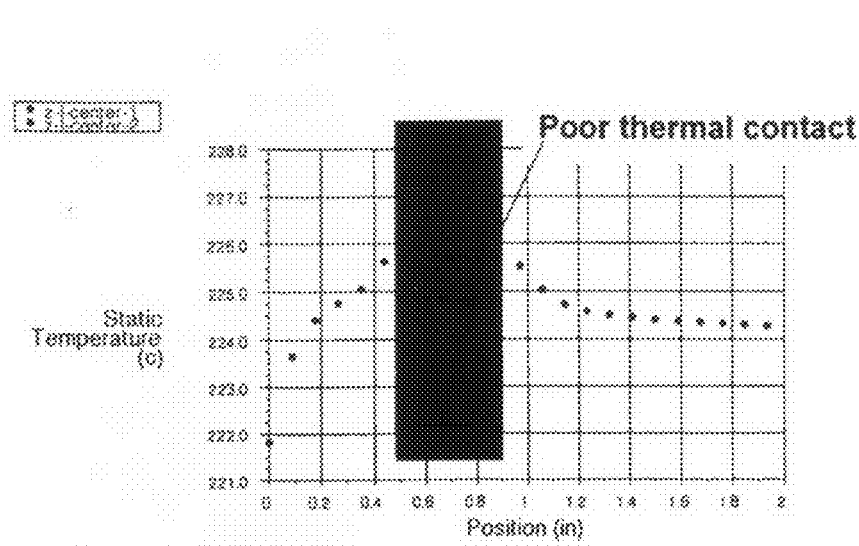
FIG. 34 is an exemplary plot of temperature profile in the catalyst bed for case A.
Figure 35:
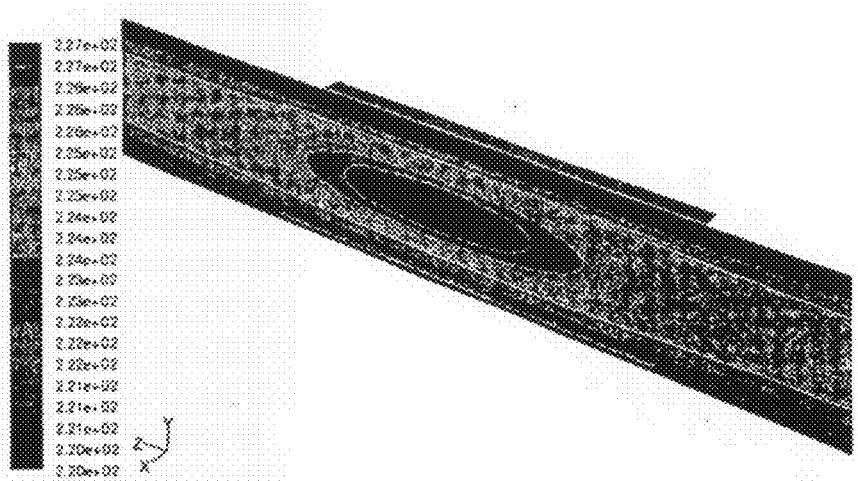
FIG. 35 is an exemplary graph showing temperature distribution at the plane cutting through the center of the catalyst bed for case A.
Figure 36:
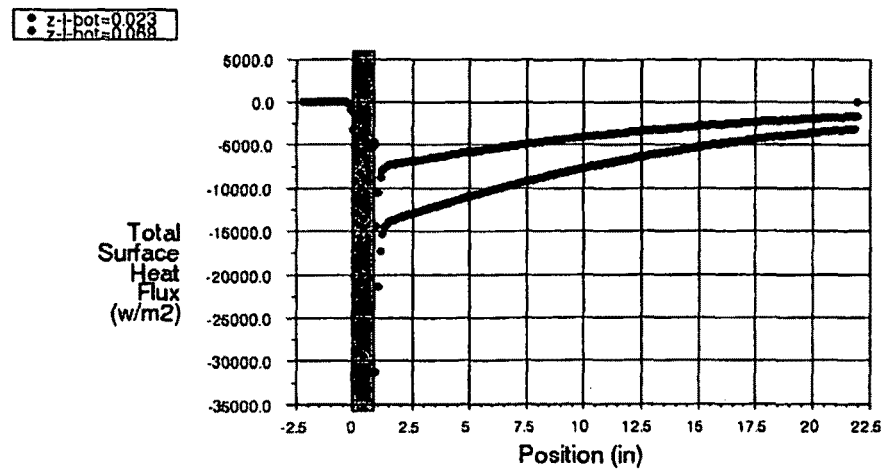
FIG. 36 is an exemplary plot of heat flux profiles on the heat transfer walls for case A.
Figure 37:
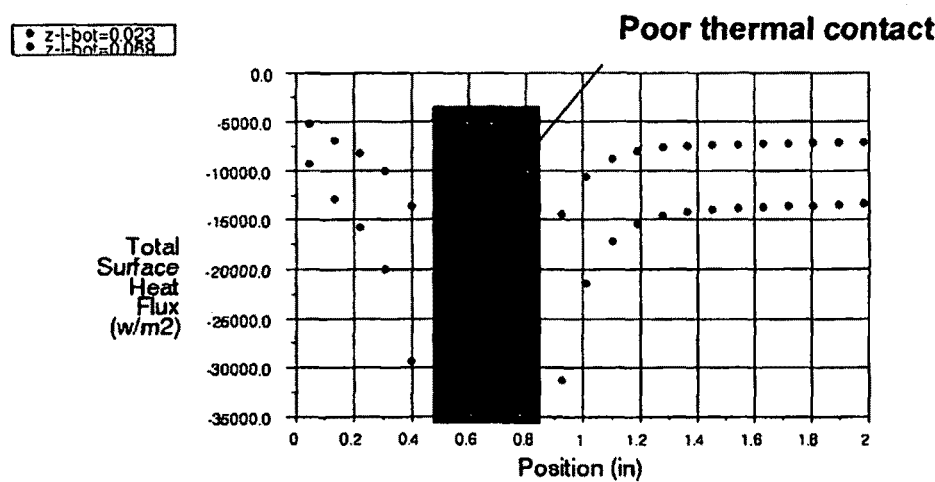
FIG. 37 is an exemplary plot of the heat fluxes on process channel walls as a function of the reactor length for case A.

The thermal resistance of various degrees between the copper corrugated insert 700 and the adjacent sheets 702 (i.e., shims) can be modeled by using adjustable thermal resistance layers (see FIG. 33). It is assumed that only heat conduction takes place in the thermal resistance layers. Some of the characteristics of these thermal layers are: (a) the thickness of a gas gap (or insulating layer between the copper waveform and the heat transfer wall) of 0.001 inches is presumed; (b) the thermal conductivity of the insulating layer is presumed to be 0.05 W/m-K; (c) the heat capacity of the layer is presumed to be 1000 J/kg-K; and (d) the density is presumed to be 8 kg/m3. In addition, the modeling approach was shaped by the following factors: (1) the location of the poor thermal contact, near the potentially high temperature region or very far from it; (2) the extent of the poor thermal contact (on whole length of the process channel or a small section of length); (3) poor thermal contact on both sides of the process channel or on a single side; and (4) the level of thermal resistance due to poor thermal contact.

With these factors in mind, four (4) cases of different thermal resistance are defined for reactors for which analytical solutions were calculated using the following premises:
A) Thermal resistance on both sides of the channel at section from 0.44 to 0.88 inches (This particular length is chosen because it brackets the maximum catalyst bed temperature of the case of perfect thermal contact between copper sheet and process channel shims);
B) Thermal resistance on one side (bottom wall) of the channel at section from 0.44 to 0.88 inches;
C) Thermal resistance on one side (bottom wall) of the channel over whole length of the reactor; and
D) Thermal resistance on one side (bottom wall) of the channel at length from 10.03 to 10.47 inches.

In addition, the following boundary conditions were adopted: (I) periodic wall boundary on two sides; (II) a constant temperature on walls facing the cooling channels is set as 220 C; (III) at inlet, the mass flux is specified to give 300 ms contact time; (IV) the ratio of $H_2$ to CO in feed is 2 and 10% $N_2$ as balance; (V) the feed temperature is set to the same value as wall temperature; and (VI) the pressure at exit is set to 350 psi. Further, the following catalyst bed characteristics were utilized: (i) a void fraction is set at approximately 0.35; and (ii) an effective thermal conductivity is set as 0.3 W/m-K. The reaction kinetics as shown in FIG. 25 are also utilized.

For the first case, case A, where the thermal resistance on both sides of the channel at section from 0.44 to 0.88 inches, the following data was determined:
CO conversion: 70.1%
CH4 selectivity: 15.5%
Maximum temperature rise: 7.1 C
Location of maximum temperature: in the catalyst bed ~0.7" from the beginning of the catalyst bed
Maximum heat flux on the heat transfer wall: 3.13 W/cm2
Location of maximum heat flux: ~0.9" from the beginning of the catalyst bed.

For the second case, case B, where the thermal resistance on one side (bottom wall) of the channel at section from 0.44 to 0.88 inches, the following data was determined:
CO conversion: 70.1%
CH4 selectivity: 15.5%
Maximum temperature rise: 5.2 C
Location of maximum temperature: in the catalyst bed ~0.7" from the beginning of the catalyst bed
Maximum heat flux on the heat transfer wall: 2.31 W/cm2
Location of maximum heat flux: ~0.7" from the beginning of the catalyst bed.

For the third case, case C, where the thermal resistance on one side (bottom wall) of the channel over whole length of the reactor, the following data was determined:
CO conversion: 70.5%
CH4 selectivity: 15.7%
Maximum temperature rise: 5.5 C
Location of maximum temperature: in the catalyst bed ~0.5" from the beginning of the catalyst bed
Maximum heat flux on the heat transfer wall: 2.64 W/cm2
Location of maximum heat flux: ~0.5" from the beginning of the catalyst bed.

For the fourth case, case D, where the thermal resistance on one side (bottom wall) of the channel at length from 10.03 to 10.47 inches, the following data was determined:
CO conversion: 70.1%
CH4 selectivity: 15.5%
Maximum temperature rise: 4.7 C
Location of maximum temperature: in the catalyst bed ~0.5" from the beginning of the catalyst bed
Maximum heat flux on the heat transfer wall: 1.47 W/cm2
Location of maximum heat flux: ~0.5" from the beginning of the catalyst bed.

As a reference case, the results for a case without thermal resistance between copper fin and process channel walls are listed below:
CO conversion: 70.0%
CH4 selectivity: 15.5%
Maximum temperature rise: 4.7 C
Location of maximum temperature: in the catalyst bed 0.5" from the beginning of the catalyst bed
Maximum heat flux on the heat transfer wall: 1.5 W/cm2
Location of maximum heat flux: 0.5" from the beginning of the catalyst bed.

In terms of the maximum temperature rise case A is the worst, but surprisingly the impact on the performance is very low. The reason is the poor contact is assumed on both sides of the process microchannel although it is only over a short section. By comparing case A and B, it is clear that the poor thermal contact on only one side of the microchannel is a much lesser concern. Furthermore, by comparing case B and C, it is concluded that if the poor thermal contact occurs only on one side of the microchannel, the extent of this poor contact won't make much difference. The case D shows that if the poor thermal contact takes place at the location far away from the potential high temperature region, it will not cause problems of global significance.

Referencing FIGS. 34-37, the temperature in the catalyst bed at centerline for case A is plotted along reactor length over the first 2 inches. The temperature peaks near 0.7 inch mark in the range of poor contact (from 0.44 to 0.88 inches) on both sides of the process microchannel. In addition, the detailed temperature distribution over the microchannel height at the plane through middle of the catalyst bed. The gray faces show the section where poor contact between corrugated insert and planar sheets is assumed. As expected the maximum temperature is observed inside of the high thermal resistance section. Still further, the heat fluxes on process microchannel walls are plotted along the reactor length for case A. For this case, where poor contact is assumed on both side of the process microchannels over the section of 0.44 to 0.88 inches, the heat flux distribution on top and bottom walls are the same. So that only the heat flux on bottom wall are plotted at locations 1 and 2. The negative sign means heat flows out of the process microchannel. Large heat flux spikes just before and after the poor contact region are observed. The same flux profiles are plotted over first 2 inch reactor length in FIG. 37.

Figure 38:
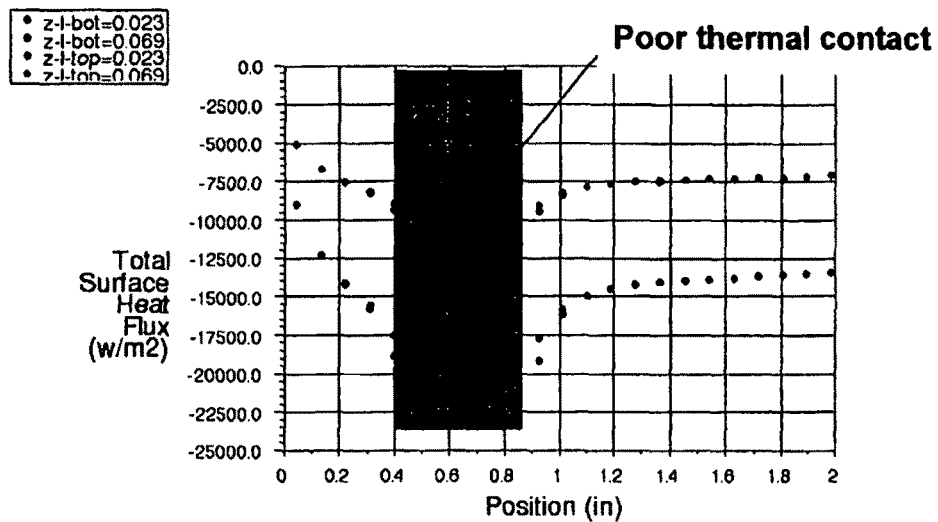
FIG. 38 is an exemplary plot of heat flux profiles heat flux profiles on heat transfer walls over first 2 inch reactor length for case B.

Referencing FIG. 38, the heat fluxes on process channel walls are plotted for case B. In case B, poor thermal contact between copper fin and channel walls is assumed on bottom side and over section of 0.44 to 0.88 inch. It is interesting to note that the maximum heat flux is actually observed on the opposite side (top wall) to the poor thermal contact location.

Figure 39:
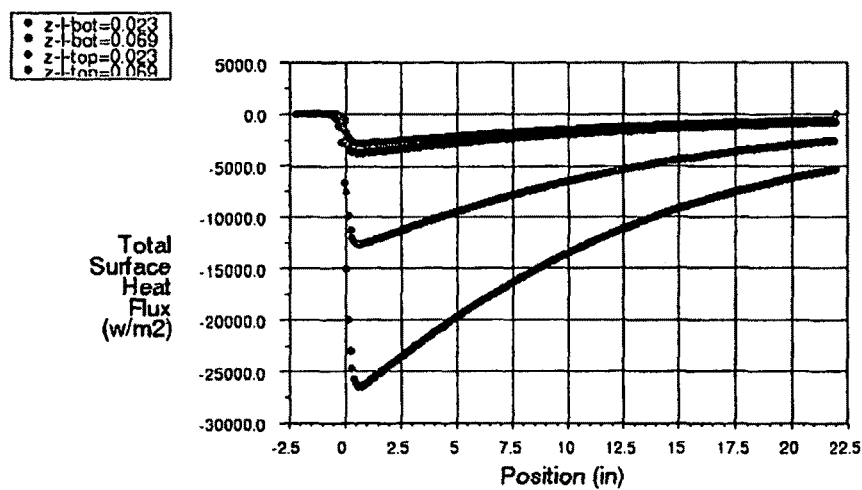
FIG. 39 is an exemplary plot of heat flux profiles on heat transfer walls for case C, with the top two curves corresponding to points 1 and 2, while the lower curves correspond to points 3 and 4, respectively.

Referencing FIG. 39, for case C where poor contact is assumed on the bottom wall over the entire length of the reactor, the heat fluxes on both sides of the microchannel walls are plotted. As expected, higher heat flux at any axial location occurs on the top wall, opposite to the poor thermal contact side.

Figure 40:
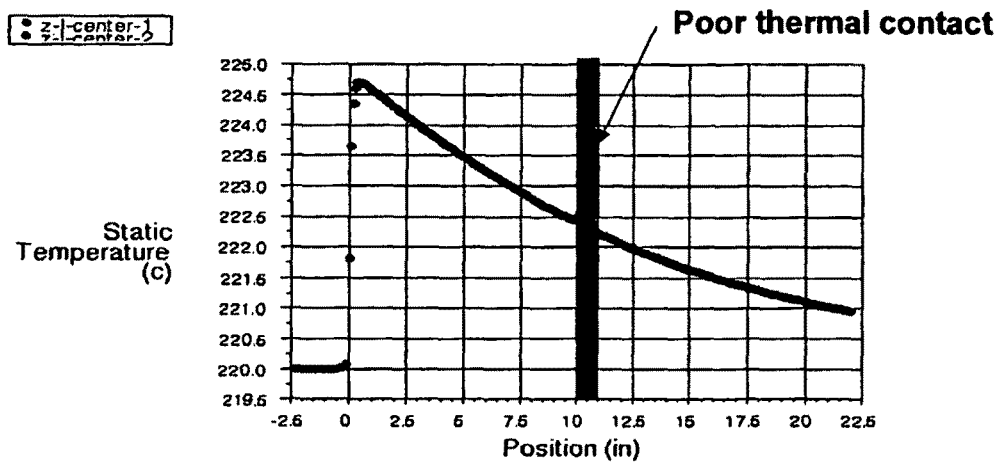
FIG. 40 is an exemplary plot of temperature profile in the catalyst bed at centerline for case D.
Figure 41:
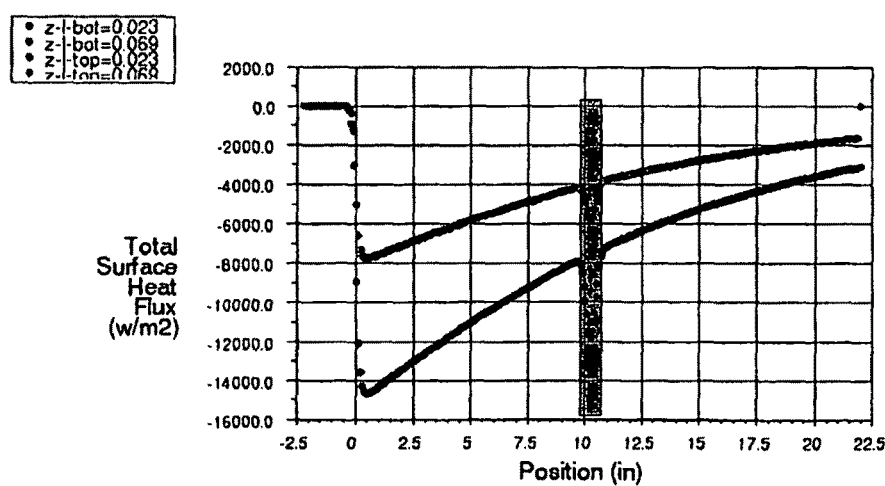
FIG. 41 is an exemplary plot of heat flux profiles on heat transfer walls for case D.

Referencing FIGS. 40 and 41, for case D, the catalyst bed temperature at centerline along the reactor length is plotted. Poor thermal contact near the middle of the reactor leads to a temperature spike of no global significance. The heat flux on microchannel walls right before and after the poor thermal contact section shows quite large spikes (see FIG. 41), but still they do not exceed the magnitude of global maximum near the inlet of the reactor.

As an unpredicted result, the use of a high thermal conductivity corrugated insert or alternate structure to bring the exothermic heat to the cooling channels allows a robust operation for less than perfect thermal contact.

The following are some exemplary numerical descriptions for the corrugated insert in accordance with the exemplary embodiments of the present invention. First, the corrugated insert may have an aspect ratio (i.e., open channel height (h [m]) to open channel width (w [m]), greater than one. The aspect ratio goes from one for a square channel to approaching zero for parallel plates. The larger the aspect ratio for the waveform the more catalyst you can use per wave form. Preferred waveforms have an aspect ratio greater than 1.5, more preferred greater than 2, more preferred still greater than 5. Second, the thermal conductivity ratio of the corrugated insert ($k_w$ [W/m/k]) to the surrounding wall interleaved between the process sheets (or shims) and the heat transfer layer ($k_s$ [W/m/k]) equals R, where larger R values are preferred. Preferred thermal conductivity ratios are greater than 1.5, more preferred greater than 2, more preferred still greater than 5, most preferred greater than 10.

$$R = \frac{k_w}{k_s}$$

Third, the corrugated wall thermal effectiveness ($\square$ [-]), assuming a rectangular cross-section of width w, length of the wall (L [m]) from the center to an adjacent wall, the heat transfer coefficient from the center of the bed to the wall ($h_b$ [W/m²/K]), it is set forth by the following equation:

$$\kappa = \frac{1}{L\sqrt{\frac{2h_b}{wk_w}}} \tanh\left(L\sqrt{\frac{2h_b}{wk_w}}\right).$$

The heat transfer coefficient is the from the center of the catalyst bed width is the effective thermal conductivity of the bed divided by the length scale, half of the bed width as defined by the distance between parallel walls of the corrugated insert that extend substantially between the heat transfer walls, $$h_b = \frac{k_{eff}}{\frac{w}{2}}$$

The wall effectiveness becomes, $$\kappa = \frac{1}{L\sqrt{\frac{4k_{eff}}{w^2 k_w}}} \tanh\left(L\sqrt{\frac{4k_{eff}}{w^2 k_w}}\right)$$

The higher the effectiveness, the more of the wall surface area one may use to control heat and extend the aspect ratio. An example of corrugated wall effectiveness factors is shown in the table below.

For copper, a total wall height of 0.5 inches (half wall height of 0.25 inches) would give an effectiveness greater than 95%. For material with lower values of thermal conductivity, such as the aluminum alloy 2024, a total wall height of 0.32 inches (half wall height of 0.16 inches) would give an effectiveness greater than 95%. These cases were based on a channel width of 1 mm, where the width is defined by the distance between the waveform fins that travel substantially between the heat transfer layers.

| Material | Corrugated insert half wall height (in) | Effectiveness factor |
|---|---|---|
| Cu (350 W/m-K) | 0.5 | 0.853 |
| | 0.25 | 0.958 |
| | 0.125 | 0.989 |
| | 0.1 | 0.993 |
| | 0.08 | 0.995 |
| | 0.05 | 0.998 |
| Aluminum alloy 2024 (122 W/m-K) | 0.5 | 0.682 |
| | 0.25 | 0.889 |
| | 0.125 | 0.969 |
| | 0.1 | 0.98 |
| | 0.08 | 0.987 |
| | 0.05 | 0.995 |

For a copper waveform selected for the FT reaction, a preferred range of corrugated insert full heights is in the range of 0.05 to 1 inch. Over this range, the effectiveness factor ranges from 85% to greater than 99%.

Following from the above description and invention summaries, it should be apparent to those of ordinary skill in the art that, while the methods and apparatuses herein described constitute exemplary embodiments of the present invention, the invention contained herein is not limited to this precise embodiment and that changes may be made to such embodiments without departing from the scope of the invention as defined by the claims. Additionally, it is to be understood that the invention is defined by the claims and it is not intended that any limitations or elements describing the exemplary embodiments set forth herein are to be incorporated into the interpretation of any claim element unless such limitation or element is explicitly stated. Likewise, it is to be understood that it is not necessary to meet any or all of the identified advantages or objects of the invention disclosed herein in order to fall within the scope of any claims, since the invention is defined by the claims and since inherent and/or unforeseen advantages of the present invention may exist even though they may not have been explicitly discussed herein.

What is claimed is:

1. A method of carrying out a Fischer-Tropsch reaction, comprising:

(a) inputting a feed stream comprising carbon containing molecules and hydrogen containing molecules to a microchannel reactor, the microchannel reactor including a corrugated insert at least partially defining a series of microchannels having an aspect ratio greater than 1.5 and housing a catalyst therein;

(b) reacting a portion of the carbon containing molecules with the hydrogen containing molecules within the microchannel reactor to form hydrocarbon molecules flowing in a process stream;

(c) removing thermal energy from the microchannel reactor using a first set of cooling microchannels in thermal communication with the microchannel reactor; and (d) removing at least a portion of the hydrocarbon molecules from the microchannel reactor.

2. The method of claim 1, wherein the microchannel reactor houses a catalyst.

3. The method of claim 1, wherein:
the catalyst includes a plurality of particles sized less than 500 microns; and
the plurality of particles within the consecutive microchannels comprise a series of parallel packed beds.

4. The method of claim 1, wherein the corrugated insert is fabricated from at least one of aluminum and copper.

5. The method of claim 1, wherein the corrugated insert is fabricated to include a series of right angles so that at least a plurality of the microchannels include rectangular cross-sections.

6. The method of claim 1, wherein a ratio of hydrogen containing molecules to carbon containing molecules input to the microchannel reactor is greater than 1.

7. The method of claim 1, wherein:
the carbon containing molecules include carbon monoxide; and
greater than thirty percent conversion of the carbon monoxide into the hydrocarbon molecules is achieved.

8. The method of claim 7, wherein:
greater than sixty percent conversion of the carbon monoxide into the hydrocarbon molecules is achieved.

9. The method of claim 7, wherein:
the act of reacting a portion of the carbon containing molecules with the hydrogen containing molecules within the microchannel reactor to form hydrocarbon molecules flowing in a process stream includes a methane selectivity less than twenty percent.

10. The method of claim 3, wherein:
a median temperature differential between two of the series of parallel packed beds is within 20 C.

11. The method of claim 3, wherein:
a temperature differential within one of the series of parallel packed beds is within 10 C.

12. The method of claim 1, wherein:
the microchannel reactor includes a pair of opposed plates that sandwich the corrugated insert; and
a median heat flux over the opposing plates is greater than 0.5 W/cm$^2$.

13. The method of claim 1, wherein:
the step of inputting the feed stream to the microchannel reactor includes flowing the feed stream at a non-Taylor flow pattern.

14. The method of claim 1, further comprising the step of screening the catalyst through a filter to retard egress of the catalyst beyond the microchannel reactor.

15. The method of claim 1, wherein the temperature variation between the reactor microchannels and the first set of cooling microchannels is between .05 and 5 degrees Celsius.

16. The method of claim 2, wherein greater than thirty percent of the available volume of the series of microchannels is occupied by the particulate catalyst.

17. The method of claim 1, wherein the corrugated insert is fabricated from at least one of aluminum and copper.

18. The method of claim 1, wherein the corrugated insert is fabricated to include a series of right angles so that at least a plurality of the microchannels include rectangular cross-sections.

19. The method of claim 1, wherein:
a Fischer-Tropsch reaction is occurring; and
a ratio of hydrogen containing molecules to carbon containing molecules input to the microchannel reactor is greater than 1.

20. The method of claim 19, wherein:
the carbon containing molecules include carbon monoxide; and
greater than thirty percent conversion of the carbon monoxide into the hydrocarbon molecules is achieved.

21. The method of claim 20, wherein:
greater than sixty percent conversion of the carbon monoxide into the hydrocarbon molecules is achieved.

22. The method of claim 20, wherein:
the act of reacting a portion of the carbon containing molecules with the hydrogen containing molecules within the microchannel reactor to form hydrocarbon molecules flowing in a process stream includes a methane selectivity less than twenty percent.

23. The method of claim 1, wherein:
the step of inputting the feed stream to the microchannel reactor includes flowing the feed stream at a non-Taylor flow pattern.

24. The method of claim 1, further comprising the step of screening the catalyst through a filter to retard egress of the catalyst beyond the microchannel reactor.

25. The method of claim 1, wherein the temperature variation between the reactor microchannels and the first set of cooling microchannels is between .05 and 5 degrees Celsius.

* * * * *